(12) United States Patent
Lukanidin et al.

(10) Patent No.: US 6,903,188 B2
(45) Date of Patent: Jun. 7, 2005

(54) NEUROGENIC COMPOSITIONS AND METHODS

(75) Inventors: Eugene Lukanidin, Copenhagen (DK); Elisabeth Marianne Bock, Charlottenlund (DK); Vladimir Berezin, Copenhagen (DK)

(73) Assignee: Prolifia Inc., Tucson, AZ (US)

( * ) Notice: Subject to any disclaimer, the term of this patent is extended or adjusted under 35 U.S.C. 154(b) by 285 days.

(21) Appl. No.: 09/781,509

(22) Filed: Feb. 12, 2001

(65) Prior Publication Data

US 2002/0099010 A1 Jul. 25, 2002

Related U.S. Application Data

(62) Division of application No. 09/393,433, filed on Sep. 10, 1999.

(51) Int. Cl.[7] .................. C07K 14/00; A61K 39/00; A61K 38/00; C12P 21/06
(52) U.S. Cl. .................. 530/350; 424/198.1; 514/2; 435/69.1
(58) Field of Search .................. 530/350; 424/198.1; 514/2; 435/69.1

(56) References Cited

U.S. PATENT DOCUMENTS

5,798,257 A 8/1998 Zain et al.
5,801,142 A 9/1998 Zain et al.

FOREIGN PATENT DOCUMENTS

WO WO 92/10200 6/1992
WO WO 95/20656 8/1995

OTHER PUBLICATIONS

Ebralidze, A., et al. (1989) "Isolation and characterization of a gene specifically expressed in different metastatic cells and whose deduced gene product has a high degree of homology to a Ca2+ –binding protein family", Genes and Development, US, Cold Spring Harbor, NY, vol. 3, 1994, pp. 1086–1093.

Klingman, D., et al. "The S100 Protein Family", Trends in Biochemical Sciences, vol. 13, No. 11, 1988, pp. 437–443.

Winningham–Major, F., et al. (1989) "Neurite Extension and Neuronal Survival Activities of Recombinant S100B Proteins That Differ in The Content and Position of Cysteine Residues", The Journal of Cell Biology, vol 109, pp. 3063–3071.

Azmitia, E.C., et al. (1990) "S–100B but not NGF, EGF, insulin or calmodulin is a CNS serotonergic growth factor", Elsevier Science Publishers B.V. (Biomedical Division).

Ebralidze, A., et al. (1989) "Isolation and characterization of a gene specifically expressed in different metastatic cells and whose deduced gene product has a high degree of homology to a $Ca^{2+}$–binding protein family", *Genes & Development 3*: 1086–1093.

Kozlova, E. N., et al. (1999) "Metastasis–Associated Mts1 (S100A4) Protein Is Selectively Expressed in White Matter Astrocytes and Is Up–Regulated After Peripheral Nerve or Dorsal Root Injury", *GLIA* 27:249–258.

*Primary Examiner*—Yvonne Eyler
*Assistant Examiner*—Janet L. Andres
(74) *Attorney, Agent, or Firm*—Scully, Scott, Murphy & Presser

(57) ABSTRACT

The present invention has found that the Mts1 protein is expressed in white matter astrocytes in the spinal cord. Such expression is significantly increased following sciatic nerve injury or dorsal root injury, particularly in astrocytes surrounding dorsal funiculus containing the central processes of the injured primary sensory neurons. The present invention has further demonstrated that Mts1 proteins administered extracellularly promote neurite outgrowth from neuronal cells. Based on these surprising findings, the present invention provides compositions and methods that are useful for the treatment of various neurological conditions characterized by death, degeneration or injury of neuronal cells.

13 Claims, 18 Drawing Sheets

(1 of 18 Drawing Sheet(s) Filed in Color)

FIG. 5A
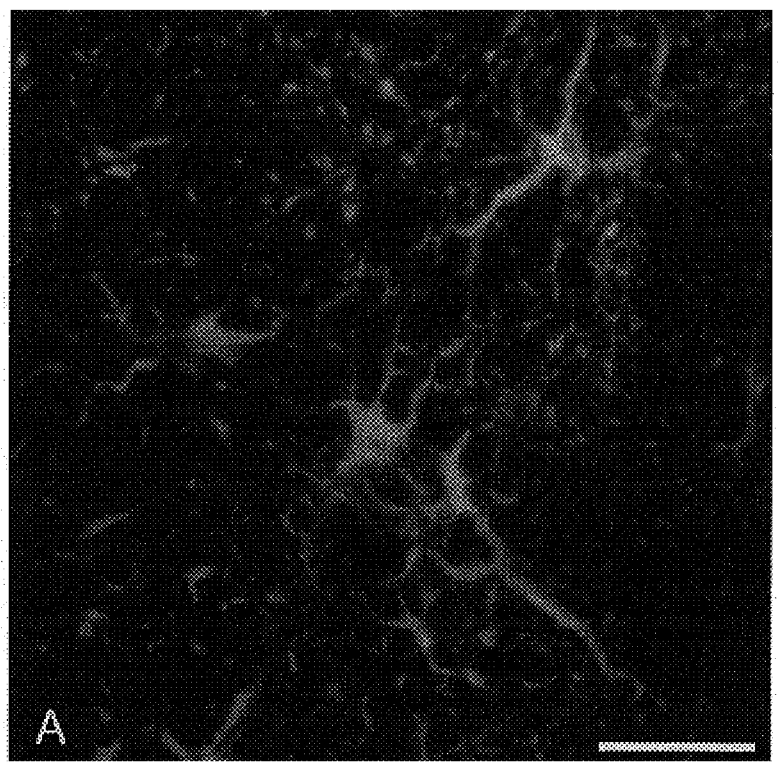
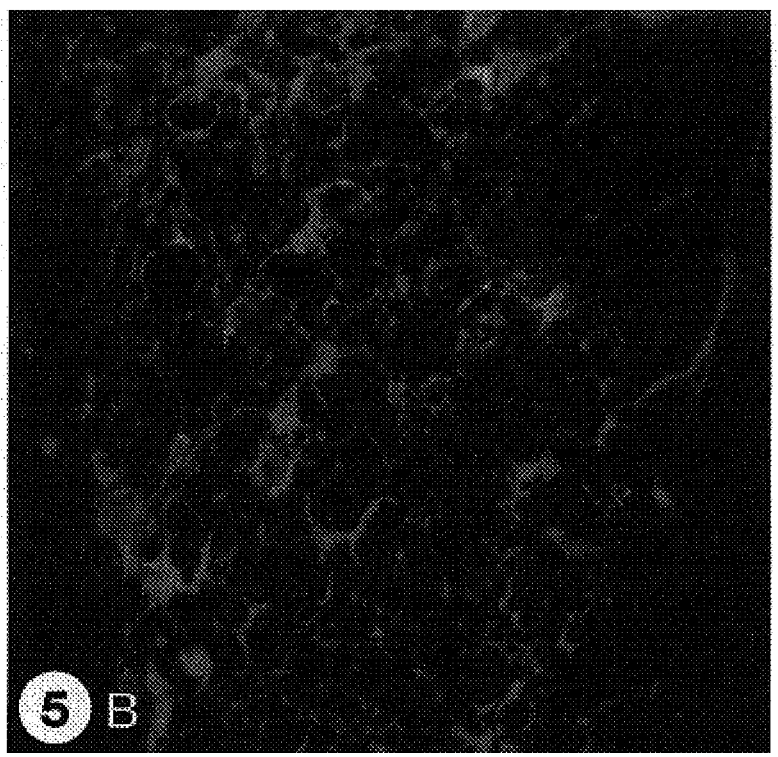
FIG. 5B

SEQUENCE LISTING

<160> NUMBER OF SEQ ID NOS: 2

<210> SEQ ID NO 1
<211> LENGTH: 101
<212> TYPE: PRT
<213> ORGANISM: Homo sapiens

<400> SEQUENCE: 1

Met Ala Cys Pro Leu Glu Lys Ala Leu Asp Val Met Val Ser Thr Phe
 1               5                  10                  15

His Lys Tyr Ser Gly Lys Glu Gly Asp Lys Phe Lys Leu Asn Lys Ser
            20                  25                  30

Glu Leu Lys Glu Leu Leu Thr Arg Glu Leu Pro Ser Phe Leu Gly Lys
        35                  40                  45

Arg Thr Asp Glu Ala Ala Phe Gln Lys Leu Met Ser Asn Leu Asp Ser
    50                  55                  60

Asn Arg Asp Asn Glu Val Asp Phe Gln Glu Tyr Cys Val Phe Leu Ser
65                  70                  75                  80

Cys Ile Ala Met Met Cys Asn Glu Phe Phe Glu Gly Phe Pro Asp Lys
                85                  90                  95

Gln Pro Arg Lys Lys
            100

<210> SEQ ID NO 2
<211> LENGTH: 101
<212> TYPE: PRT
<213> ORGANISM: Mus musculus

<400> SEQUENCE: 2

Met Ala Arg Pro Leu Glu Glu Ala Leu Asp Val Ile Val Ser Thr Phe
 1               5                  10                  15

His Lys Tyr Ser Gly Lys Glu Gly Asp Lys Phe Lys Leu Asn Lys Thr
            20                  25                  30

Glu Leu Lys Glu Leu Leu Thr Arg Glu Leu Pro Ser Phe Leu Gly Lys
        35                  40                  45

Arg Thr Asp Glu Ala Ala Phe Gln Lys Val Met Ser Asn Leu Asp Ser
    50                  55                  60

Asn Arg Asp Asn Glu Val Asp Phe Gln Glu Tyr Cys Val Phe Leu Ser
65                  70                  75                  80

Cys Ile Ala Met Met Cys Asn Glu Phe Phe Glu Gly Cys Pro Asp Lys
                85                  90                  95

Glu Pro Arg Lys Lys
            100

NEUROGENIC COMPOSITIONS AND METHODS

The present application is a divisional of Ser. No. 09/393,433, filed Sep. 10, 1999.

FIELD OF INVENTION

The present invention relates to the discovery of the role of the Mts1/S100A4 protein in the neural system. Compositions and methods are provided that are useful for stimulating growth of neuronal cells and treating neuronal damage caused by disease or trauma.

BACKGROUND OF THE INVENTION

The S100 proteins comprise a large family of calcium-binding proteins, some of which are expressed at high levels in the nervous system. The S100 proteins have been implicated in a wide variety of functions, such as modulation of enzyme function, alteration of cytoskeletal dynamics, cell adhesion and control of cell cycle progression (Schafer et al., *Trends Biochem Sci* 21: 134–140, 1996). Expression of S100 protein has been shown to be associated with invasive potential and metastatic spread of tumor cells (Inoue et al., *Virchows Arch* A422: 351–355, 1993).

The primary structure of S100 proteins is highly conserved (Kligman et al., *TIBS* 13: 437–443, 1988; and Schaefer et al., *TIBS* 21: 134–140, 1996). In solutions S100 proteins easily form dimers and cystein residues are not necessary for the noncovalent dimerization of S100 (Mely et al., *J. Neurochemistry* 55: 1100–1106, 1990; Landar et al., *Biochim. Biophys. Acta* 1343: 117–129, 1997; and Raftery et al., *J Am. Soc. Mass Spectrom.* 9: 533–539, 1988). The tertiary structure of S100 proteins has been characterized (Kilby et al., *Structure* 4: 1041–1052, 1996; Smith et al., *Structure* 6: 211–222, 1998; Sastry et al., *Structure* 15: 223–231, 1998; and Matsumura et al, *Structure* 6: 233–241, 1998). Each S100 monomer contains two EF-hand calcium binding domains (Schafer et al., *TIBS* 21: 134–140, 1996). Calcium binding results in a conformational alteration and exposure of a hydrophobic patch via which S100 proteins interact with their targets (Smith et al, *Structure* 6: 211–222, 1998; Sastry et al, *Structure* 15: 223–231, 1998; Matsumura et al, *Structure* 6: 233–241, 1998; and Kilby et al., *Protein Sci.* 6: 2494–2503, 1997).

Intracellular and extracellular activities of S100 proteins have also been described (McNutt, *J Cutan. Pathol.* 25: 521–529, 1988). Intracellular S100 proteins interact with numerous target proteins and modulate multiple cellular processes regulating cell growth, differentiation, metabolism and cytoskeletal structure (Zimmer et al., *Brain Res. Bulletin* 37: 417–429, 1995; Schafer et al., *TIBS* 21: 134–140, 1996; Donato, *Cell Calcium* 12: 713–726, 1991; and Lukanidin et al., In: Gunter U, Birchmeier W, eds. *Current Topics in Microbiology and Immunology: Attempts to Understand Metastasis Formation II*. Berlin, Heidelberg: Springer-Verlag 213/II, 171–195, 1996). Extracellular disulfide-linked dimers of S100B protein have been reported to stimulate neurite outgrowth in primary cultures of cerebral cortex neurons (Kligman et al., *TIBS* 13: 437–443, 1988). Such activity has also been reported for oxidized form of the recombinant S100B protein (Winningham-Major et al., *J. Cell Biol.* 109: 3063–3071, 1989).

The mts1/S100A4 gene, a member of the S100 gene family, was isolated as a gene specifically expressed in metastatic murine tumor cell lines (Ebralidze et al., *Genes Dev.* 3: 1086–1092, 1989). Studies of Mts1-transfected non-metastatic murine cell lines and Mts1 transgenic mice both indicate that Mts1 plays an important role in tumor progression (Grigorian et al., *Gene* 135: 229–238, 1993; Takenaga et al., *Oncogene* 14: 331–337, 1997; Ambartsumian et al., *Oncogene* 13: 1621–1630, 1996; and Davies et al., *Oncogene* 13: 1631–1637, 1996). Mts1 has also been shown to affect the cytoskelton and cell motility (Takenaga et al., *Jpn. J Cancer Res.* 85: 831–839, 1994) via association with stress fibers (Gibbs et al., *J. Biol. Chem.* 269: 18992–18999, 1994). The heavy chain of non-muscle myosin (MHC) has been identified as a target for the Mts1 protein (Kriajevska et al., *J. Biol. Chem.* 239: 19679–19682, 1994).

The present invention identifies, for the first time, the neurogenic function of the Mts1 protein. Accordingly, the present invention provides novel compositions and methods useful for stimulating neurite growth in the treatment of neural damage caused by disease or physical trauma.

SUMMARY OF THE INVENTION

One embodiment of the present invention provides an isolated functional derivative of an Mts1 protein. A preferred functional derivative of an Mts1 protein is Mts1 del75.

Another embodiment of the present invention provides an isolated multimeric Mts1 protein complex. Such complex includes at least three Mts1 protein molecules or functional derivatives thereof.

In another embodiment, the present invention provides pharmaceutical compositions which include an isolated functional derivative of an Mts1 protein, or a multimeric Mts1 protein complex, and a pharmaceutically acceptable carrier. The pharmaceutical compositions can also include one or more neurotropic factors.

In a further embodiment, the present invention provides methods of stimulating growth of neuronal cells by administering an Mts1 protein or a functional derivative thereof.

In a further embodiment, the present invention provides methods of treating neurological conditions in a subject by administering to the subject a therapeutically effective amount of an Mts1 protein or a nucleotide sequence encoding an Mts1 protein. The methods of the present invention can be employed in the treatment of a variety of neurological conditions characterized by neuronal degeneration, neuronal death or injury caused by disease, physical trauma or ischemic conditions. Such neurological conditions include Parkinson's disease, Down's Syndrome, Alzheimer's disease, stroke, cardiac arrest, sciatic crush, spinal cord injury, damaged sensory neurons in dorsal root ganglia and other tissues, as well as degenerative diseases of the retina.

BRIEF DESCRIPTION OF DRAWINGS

The file of this patent contains at least one drawing executed in color as determined by the U.S. Patent and Trademark Office. Copies of this patent with color drawing(s) will be provided by the Patent and Trademark Office upon request and payment of the necessary fees.

FIGS. 5A–5B depict double labeling with antibodies to Mts1 and GFAP (A), and double labeling with antibodies to Mts1 and the microglia/macrophage marker ED1 (B) in the degenerating dorsal funiculus two months after transection of the L4 and L5 dorsal roots. Mts1-IR (A,B,green) is confined to GFAP-positive astrocytes (A,red), but completely absent from ED1-positive cells (B,red). Bar=50 µm.

FIG. 11D depicts Commassie Blue staining of SDS-PAGE (a) and Western blotting analysis (b) of peaks I, II and III of wt Mts1. Immuno-staining was performed with affinity purified antibodies against Mts1. Lanes 1–4—peak I (fractions 3–6); Lanes 5–7—peak II (fractions 8–10); Lanes 8–10—peak III (fractions 14–16).

DETAILED DESCRIPTION OF EMBODIMENTS

Figure 1:
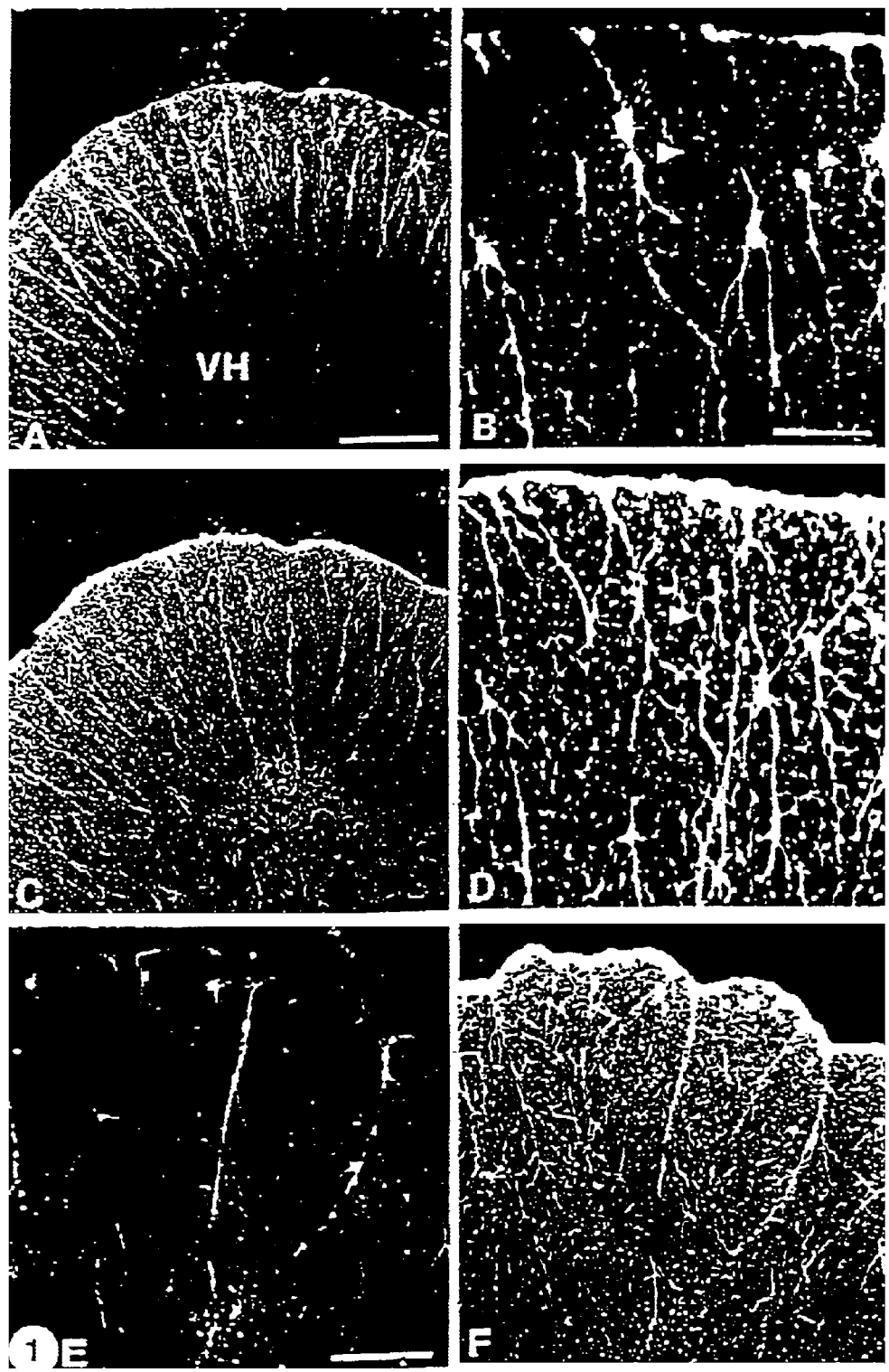
FIG. 1 depicts Mts1-immunoreactivity (IR) (A,B,E) and GFAP-IR (C,D,F) in the normal white matter of LA. (A) shows Mts1-IR in the ventral and lateral funiculi, with exclusive expression in white matter. Double labeling with antibodies to Mts1 and GFAP shows that Mts1 is localized to astrocytes (B,D) and is predominantly expressed in the cell bodies (B), while intense GFAP-IR is observed in processes as well (D). Arrowheads indicate cells that were labeled with anti-GFAP antibodies (D), but not with antibodies to Mts1 (B). (E) shows a few Mts1-positive cell bodies as well as Mts1-positive processes in paramedian septa of the dorsal funiculus in C3 (E), despite widespread GFAP-IR (F). Bar=200 µm (A,C), 50 µm (B,D), 100 µm (E,F).

The Mts1/S100A4 protein is known in the art to be involved in the control of cell proliferation and metastasis of tumor cells. The present inventor has surprisingly discovered a function of the Mts1/S100A4 protein that is associated with the nervous system.

Specifically, it has been discovered by the present inventor that the Mts1 protein is expressed in white matter astrocytes in the spinal cord. In accordance with the present invention, it has also been found that sciatic nerve injury as well as dorsal root injury induces a marked and prolonged increase in the level of the Mts1 protein, particularly in astrocytes surrounding dorsal funiculus containing the central processes of the injured primary sensory neurons. Additionally, the present invention demonstrates that Mts1 proteins administered extracellularly promote neurite outgrowth from neuronal cells.

Accordingly, the present invention employs the neurogenic activity of the Mts1 protein and provides compositions and methods that are useful for the treatment of various neurological conditions characterized by the death, degeneration or injury of neuronal cells.

By "neurogenic activity" is meant a biological activity that induces, stimulates, or enhances the growth, maintains the survival, or prevents the death of the neuronal cells of the central and peripheral nervous system of a mammal. The activity can manifest as differentiation of neurons, extension of neuritic processes (i.e., outgrowth or elongation of neurites), or innervation of neuritic processes into a tissue.

One embodiment of the present invention provides an isolated functional derivative of an Mts1 protein.

"An Mts1 protein" as used herein, refers to a wild type Mts1 protein of a mammalian origin, such as human, murine and the like. Preferred Mts1 proteins of the present invention include human Mts1 (SEQ ID NO: 1) and murine Mts1 (SEQ ID NO: 2), which are also described in U.S. Pat. No. 5,801,142 and Ebralidze et al., Genes Dev. 3: 1086–1092, 1989, respectively.

"A functional derivative of an Mts1 protein" refers to a modified Mts1 protein having one or more amino acid substitutions, deletions or insertions, which retains substantially the neurogenic activity of a wild type Mts1 protein. By substantially is meant at least about 35%, preferably, at least about 40%.

In accordance with the present invention, a preferred functional derivative of a wild type Mts1 protein is Mts1-del75, i.e., deletion of the Tyr residue at the position 75 in human or murine Mts1 protein, or the corresponding Tyr in any other mammalian Mts1 proteins. It has been determined by the present inventor that Mts1-del75 is able to form polymers and confers about 70% neurogenic activity compared to a wild type Mts1 protein. Another Mts1 mutant which has all four Cysteine residues mutated to Serine (designated herein as "4S") retains about 40% of the neurogenic activity of a wild type Mts1 protein.

Those skilled in the art can use any of the well-known molecular cloning techniques to generate Mts1 derivatives having one or more amino acid substitutions, deletions or insertions. See, for example, Current Protocols in Molecular Cloning (Ausubel et al., John Wiley & Sons, New York). Once a modified Mts1 protein is made, such protein can be tested in functional assays to determine whether such modified protein exhibits neurogenic activity.

In accordance with the present invention, the neurogenic activity of an Mts1 protein or protein complex can be determined by a number of assays. A typical functional assay is described in Example 2 hereinbelow. Briefly, an Mts1 protein is added in various doses in the culture medium of neuronal cells, such as hippocampal neuronal cells, or PC-12 cells. The cells can be kept exposed to the protein for a certain period of time and the outgrowth of neurites from the cultured cells are monitored. Parameters such as the length of the longest neurite extension, the number of neurite branches per cell, and the total neurite length per cell, are measured. The determination as to whether a modified Mts1 protein possesses neurogenic activity can be made by comparing these parameters with those values of a wild type Mts1 protein and those values of a control protein without neurogenic activity. Other assays which can be employed for such determination include, e.g., the standard assay of endothelial cell motility in Boyden Chamber.

Another embodiment of the present invention provides an isolated multimeric Mts1 protein complex.

In accordance with the present invention, it has been found that the neurogenic activity of Mts1 is associated with the polymeric forms composed of three or more Mts1 protein molecules. Not intending to be bound by any theory, it is proposed herein that the Mts1 protein mediates its neurogenic effects via a cell surface receptor which recognizes polymeric forms of the Mts1 protein.

According to the present invention, the terms "a multimeric Mts1 protein complex" and "a polymeric Mts1 protein complex" as used herein refer to a complex having at least three, i.e., three or more, molecules of an Mts1 protein or a functional derivative of an Mts1 protein. The complex can have a Mw of at least about 30 kd, more preferably, at least about 100 kd, and up to about 200 kd, as determined by, e.g., size-exclusion chromatography.

In accordance with the present invention, the Mts1 protein molecules in the complex can be held together by covalent and/or non-covalent interactions among Mts1 protein molecules. For example, there are four Cys residues in both human and murine Mts1, which can form intramolecular disulfide bonds under appropriate conditions thereby leading to formation of polymeric Mts1 complexes. The present invention also contemplates polymeric Mts1 complexes formed by chemical cross-linking reagents. Chemical cross-linking reagents and use thereof in making multimeric protein complexes are well known in the art. In accordance with the present invention, a Mts1 protein complex having neurogenic activity can be formed through non-covalent interactions among Mts1 molecules as well. For example, the present invention provides that Mts1-4S, while unable to form any intramolecular or intermolecular disulfide bonds, is able to form polymers and confers neurogenic activity at a level of about 40% of that of a wild type Mts1 protein.

The Mts1 complexes of the present invention can be isolated by a variety of methods. For example, an Mts1 protein can be dissolved in solution under conditions that favor the formation of polymers, e.g., a saline solution of about 0.15 M NaCl, pH7.5 with a Mts1 concentration higher than, preferably, 1 mg/ml. Afterwards, the solution can be subjected to an appropriate chromatography procedure using, e.g., Size-Exclusion-Column euqilibrated with a TND buffer (50 mM Tris-HCl, 150 mM NaCl, 1 mM DTT, pH 7.5). The Mts1 protein can be eluted using the same TND buffer, and fractions containing polymers can be collected and separated from the fractions containing dimers. Such procedure is described in Example 3 hereinbelow. An Mts1 protein can also be subjected to chemical cross-linking prior to chromatography or fraction procedures. Those skilled in the art can make modifications when appropriate and necessary. in another embodiment, the present invention provides pharmaceutical compositions which include a functional derivative of an Mts1 protein, or an isolated multimeric Mts1 protein complex composed of at least three Mts1 protein molecules.

The pharmaceutical compositions of the present invention can be employed to promote neuronal cell growth or maintain the survival of neuronal cells in the treatment of neurological conditions characterized by the death, degeneration or injury of neuronal cells.

The functional derivative or the protein complex of an Mts1 protein for use in the pharmaceutical compositions can be modified according to procedures known in the art in order to enhance penetration of the blood-brain barrier. For example, U.S. Pat. No. 5,604,198 discloses that a molecule can be conjugated to a hydrophobic carrier which enhances the permeability of the blood brain barrier (BBB). WO 90/14838 teaches chemical modifications of a protein by increasing lipophilicity, altering glycosylation or increasing the net positive charge in order to enhance the BBB permeability of the protein.

According to the present invention, the pharmaceutical compositions can also include one or more neurotropic factors.

Neurotropic factors are proteins which promote the survival of neurons, some of which are also capable of promoting neurite outgrowth and glial cell restoration or inducing cells to secrete other neurotropic factors. Preferred neurotropic factors for use in the present pharmaceutical compositions are those to which a broad range of cell types respond. Examples of preferred neurotropic factors include members of the BDNF/NGF family, such as bFGF (basic fibroblast growth factor), aFGF (acidic fibroblast growth factor), CNTF (ciliary neurotrophic factor), NGF (nerve growth factor), BDNF (brain-derived neurotrophic factor), GDNF (glial cell line-derived neurotrophic factor), NT-3 (neurotrophin-3), NT-4/5 (neurotrophin 4/5), IGF-1 (insulin growth factor-I), IGF-II (insulin growth factor-II), and functional peptide fragments thereof. Human neurotropic factors and functional derivatives are preferred.

The active ingredients of the pharmaceutical compositions are preferably provided in a pharmaceutically acceptable carrier. The carrier can be liquid, semi-solid, e.g. pastes, or solid carriers. Except insofar as any conventional media, agent, diluent or carrier is detrimental to the recipient or to the therapeutic effectiveness of the active ingredients contained therein, its use in the pharmaceutical compositions of the present invention is appropriate. Examples of carriers include oils, water, saline solutions, gel, lipids, liposomes, resins, porous matrices, binders, fillers and the like, or combinations thereof. The carrier can also be a controlled release matrix which allows a slow release of the active ingredients mixed or admixed therein. Examples of such controlled release matrix material include, but are not limited to, sustained release biodegradable formulations described in U.S. Pat. No. 4,849,141 to Fujioka et al., U.S. Pat. No. 4,774,091 to Yamashira, U.S. Pat. No. 4,703,108 to Silver et al., and Brem et al. (*J. Neurosurg.* 74: 441–446, 1991), all of which are incorporated herein by reference.

In accordance with the present invention, a Mts1 functional derivative or an Mts1 polymeric complex can be combined with the carrier in solutions or in solid phase, preferably in a manner that favors the stablization of the polymeric conformation of the Mts1 protein. If the mixing step is to be performed in liquid phase, Mts1 proteins can be dissolved together with a carrier in solutions such as saline (about 0.15 M NaCl pH7.5) with an Mts1 concentration of higher than, preferably, 1 mg/ml. If the mixing is to be performed in solid phase, the Mts1 polymeric proteins can be freeze-dried first to preserve the polymeric conformation, then admixed with the carrier. The mixture can be made in formulations suitable for injections, implantations, inhalations, ingestions and the like.

In a further embodiment, the present invention provides methods of stimulating growth of neuronal cells by administering an Mts1 protein, a functional derivative of an Mts1 protein, or a protein complex thereof, to such neuronal cells.

According to the present invention, an Mts1 protein or a functional derivative or complex thereof, can be administered to neuronal cells that are cultured in vitro. This aspect of the invention is particularly useful in regeneration of neurons for autotransplantation or neuron replacement as an alternative treatment procedure to brains of patients with neurological disorders. Techniques of culturing neurons in vitro fare known in the art and are described in, e.g., U.S. Pat. Nos. 5,483,892, 5,753,506, 5,898,066, and 5,667,978, Mou et al. *J. Comp. Neurol.* 386: 529 (1997), and Tan et al. Cell Transplant 5: 577 (1996), the teachings of which are incorporated herein by reference.

In a further embodiment, the present invention provides methods of treating neurological conditions in a subject by administering to the subject a therapeutically effective amount of an Mts1 protein, a functional derivative thereof, or a nucleotide sequence encoding an Mts1 protein.

The methods of the present invention can be employed in the treatment of a variety of neurological conditions characterized by neuronal degeneration, neuronal death or injury caused by disease, physical trauma or ischemic conditions. Such neurological conditions include Parkinson's disease, Alzheimer's disease, Down's Syndrome, stroke, cardiac arrest, sciatic crush, spinal cord injury, multiple sclerosis, peripheral neuropathies associated with diabetes, motorneuron diseases, damaged sensory neurons in dorsal root ganglia and other tissues, as well as degenerative diseases of the retina.

By "treating" is meant prevent or inhibit neuronal degeneration or neuronal death, promoting or stimulating neuronal growth such that the symptoms of the disease condition are prevented or alleviated.

In accordance with the methods of the present invention, an Mts1 protein can be first treated to enrich the polymeric forms, or can be used directly, as certain percentage of the molecules spontaneously associate with each other to form polymers in solution. An Mts1 protein or a functional derivative thereof can be modified in order to enhance penetration of the blood-brain barrier as described hereinabove.

Nucleic acid sequences encoding an Mts1 protein can also be employed in the methods of the present invention. Such sequences are preferably provided in an expression vector. Expression vectors for use in the present methods include any appropriate gene therapy vectors, such as nonviral (e.g., plasmid vectors), retroviral, adenoviral, herpes simplex viral, adeno-associated viral, polio viruses and vaccinia vectors. Examples of retroviral vectors include, but are not limited to, Moloney murine leukemia virus (MoMuLV), Harvey murine sarcoma virus (HaMuSV), murine mammary tumor virus (MuMTV), and Rous Sarcoma Virus (RSV)-derived recombinant vectors. Multiple teachings of gene therapy are available to those skilled in the art, e.g., W. F. Anderson (1984) "Prospects for Human Gene Therapy" *Science* 226: 401–409; S. H. Hughes (1988) "Introduction" *Current Communications in Molecular Biology* 71: 1–12; T. Friedman (1989) "Progress Toward Human Gene Therapy" *Science* 244: 1275–1281 and W. F. Anderson (1992) "Human Gene Therapy" *Science* 256: 608–613. Preferred vectors include neurotropic vectors such as herpes simplex viral vectors (U.S. Pat. No. 5,673,344 to Kelly et al. and adenoviral vectors (Barkats et al., *Prog. Neurobiol.* 55: 333–341, 1998).

Mts proteins or Mts1-encoding nucleic acid molecules can be used alone or in conjunction with one or more neurotropic factors described hereinabove, including members of the BDNF/NGF family such as bFGF, aFGF, CNTF, NGF, BDNF, GDNF, NT3, NT4/5, IGF-1 and IGF-II, as well as the functional peptide fragments identified thereof. Human neurotropic factors are preferred for treating a human subject.

The therapeutically active ingredients, i.e., Mts1 proteins or nucleic acid molecules, alone or in conjunction with neurotropic factors, can be combined with a pharmaceutically acceptable carrier and prepared in formulations suitable for injections, implantations, inhalations, ingestions and the like. Pharmaceutically acceptable carriers are described hereinabove and include oils, water, saline solutions, gel, lipids, liposomes, resins, porous matrices, binders, fillers and the like, or combinations thereof.

According to the present invention, these therapeutic compositions can be administered to the subject being treated by standard routes, including the oral, ophthalmic nasal, topical, transdermal, parenteral (e.g., intravenous, intraperitoneal, intradermal, subcutaneous or intramuscular), intracranial, intracerebral, intraspinal, intravaginal, intrauterine, or rectal route. Depending on the condition being treated, one route may be preferred over others, which can be determined by those skilled in the art. For example, topical route can be chosen when the target area includes tissues or organs readily accessible by topical application, such as neurological conditions of the eye or the facial tissue. For certain conditions, direct injection or surgical implantation in the proximity of the damaged tissues or cells may be preferred in order to avoid the problems presented by BBB. Successful delivery to CNS (Central Nervous System) by direct injection or implantation has been documented. See, e.g., Otto et al., *J. Neurosci. Res.* 22: 83–91 (1989); Goodman & Gilman's *The Pharmacological Basis of Therapeutics*, 6$^{th}$ ed, pp244; Williams et al., *Proc. Natl. Acad. Sci. USA* 83: 9231–9235 (1986); and Oritz et al., *Soc. Neurosci. Abs.* 386: 18 (1990).

According to the present invention, the therapeutic ingredients are preferably administered to the subject in need thereof as early as possible after the neuronal injury or death occurs in order to achieve the best therapeutic efficacy.

The amount of an Mts1 protein, a functional derivative, or an Mts1-encoding nucleic acid molecule to be therapeutically effective depends on the disease state or condition being treated and other clinical factors, such as weight and physical condition of the subject, the subject's response to the therapy, the type of formulations and the route of administration. The precise dosage to be therapeutically effective and non-detrimental to the subject can be determined by those skilled in the art. As a general rule, the therapeutically effective amount of Mts1 protein can be in the range of about 0.01 mg to about 10 mg per kilogram of body weight; preferably, in the range of about 0.1 mg to about 5 mg per kilogram of body weight. The therapeutically effective dosage of an Mts1 protein can be in the range of about 0.5 μg to about 2 mg per unit dosage form. A unit dosage form refers to physically discrete units suited as unitary dosages for mammalian treatment: each unit containing a pre determined quantity of the active material calculated to produce the desired therapeutic effect in association with any required pharmaceutical carrier. The methods of the present invention contemplate single as well as multiple administrations, given either simultaneously or over an extended period of time.

This invention is further illustrated by the following examples, which are not to be construed in any way as imposing limitations upon the scope thereof. The terms and expressions which have been employed in the present disclosure are used as terms of description and not of limitation, and there is no intention in the use of such terms and expressions of excluding any equivalents of the features shown and described or portions thereof. It is to be understood that various modifications are possible within the scope of the invention. All the publications mentioned in the present disclosure are incorporated herein by reference.

EXAMPLE 1

Mts1 Expression is Up-Regulated After Peripheral or Dorsal Root Injury

Introduction of the Experimental Model

The primary sensory neurons of the spinal cord with their cell bodies located peripherally, send out dichotomizing processes, one branch projecting peripherally to innervate peripheral tissues and organs, the other branch entering the CNS via spinal dorsal roots. Dorsal root axons terminate in a specific pattern in the gray matter of the dorsal horn. In addition, collaterals of myelinated primary sensory axons ascend in the dorsal funiculus of the white matter to the lower brainstem where they terminate in the dorsal column nuclei.

Injury to the dorsal root (rhizotomy) and injury to the peripheral branches produce markedly different morphological and molecular changes in the affected neurons. However, both injuries are associated with prominent responses in surrounding non-neuronal cells in the CNS, particularly astrocytes and microglia/macrophages. Injury to the peripheral branches, e.g. by section of the sciatic nerve, induces degenerative as well as growth-associated changes (transganglionic changes) in the central terminals and axons of the injured neurons (Aldskogius et al., *Oxford Univ Press.* pp 363–383, 1992; Woolf et al., *Neurosci* 34: 465–4678, 1990; and Woolf et al., *J Comp Neurol* 360: 121–134, 1995). Concomitantly, microglial cells proliferate (Gehrmann et al., *Restor Neurol Neurosci* 2: 181–198, 1991; Eriksson et al., *Ex Brain Res* 114: 393–404, 1993; and Persson et al., *Primary Sensory Neuron* 1: 47–64, 1995), and express various inflammatory mediators (Liu et al., *Neurosci* 68: 167–179, 1995), while astrocytes upregulate the expression of their major intermediate filament, glial fibrillary acidic protein (GFAP) (Gilmore et al., *Glia* 3: 342–349, 1990) but do not proliferate. Injury to the central primary sensory process by section of the dorsal root, results in complete disintegration (Wallerian degeneration) of the segment of the axon no longer in continuity with the parent cell body. The non-neuronal response to this degeneration includes proliferation of microglia, that gradually develops into macrophages, as well as proliferation of astrocytes and a rapid increase in the expression of GFAP in astrocytes (Liu et al., *Glia* 23: 221–238, 1998).

Materials and Methods

Thirty-two adult, female, Sprague-Dawley rats (160–180 g body weight) were used for the study. Prior to surgery and perfusion, animals were anaesthetized with chloral hydrate (35 mg/kg body weight i.p.).

Twelve animals were subjected to section of the left sciatic nerve at midthigh level. Two animals (n=2) were analyzed at each postoperative survival time (1 day, 2 days, 3 days, 7 days, 1 month and 2 months). In 18 animals, the left lumbar dorsal roots L4 and L5 were exposed via a partial laminectomy and sectioned close to the corresponding dorsal root ganglia (n=3 for each postoperative survival time). At the indicated postoperative survival time, the animals were perfused via the left ventricle first with saline (37° C.) followed by a solution of 4% formaldehyde (w/v) and 14% saturated picric acid (v/v) in a 0.15 M phosphate buffer (pH 7.4, 4° C.). Two intact control animals were perfused in the same way. The L4-LS and C3 spinal cord segments as well as the brainstem were removed, postfixed for about one and half hours, and subsequently stored overnight in refrigerator. Serial, 14 μm transverse sections were cut on a cryostat and processed for immunofluorescence. In addition, sets of sections were cut at 5 μm to provide material for optimal microphotography.

Sections were briefly air-dried and washed in phosphate buffer for 5–10 mins prior to incubation in BSA and 0.3% Triton X100 (Sigma, USA) for one hour at room temperature. Sections were incubated overnight at 4° C. with antibodies against Mts1 (rabbit polyclonal, 1:1000). The immune complex was visualized with FITC-conjugated sheep anti-rabbit IgG (Jackson, 1:40). For double labeling experiments, anti-Mts1 antibodies were combined with one of the following antibodies: (1) anti-GFAP (astrocytes, mouse monoclonal (Serotec, U.K.), 1:3), (2) OX42 (microglia, mouse monoclonal (Serotec, U.K.), 1:600), or (3) ED1 (phagocytic microglia/macrophages, mouse monoclonal (Serotec, U.K.), 1:400). The cell marker antibodies were visualized with rhodamine (TRITC)-conjugated anti-mouse IgG. Sections were viewed and photographed in a Nikon Eclipse fluorescence microscope equipped with filter for simultaneous examination of FITC and TRITC fluorescence.

Intact Control Animals

Mts1 immunoreactivity (IR) was observed in the white matter of the L4 and C3 segments of the spinal cord as well as in the brainstem. The most prominent staining appeared in the ventral and lateral funiculi as processes radiating from the subpial region and towards the gray matter, leaving, however, its immediate white matter surroundings free from Mts1-IR (FIG. 1, A and B). Mts1-IR cell bodies were typically located in the subpial region as well as about midway between this region and the gray matter. Double labeling with glial cell markers showed colocalization between Mts1 and anti-GFAP (FIG. 1, B and D), but a minority of GFAP-positive cells was not labeled with Mts1. However, astrocytes which did express Mts1, showed a more complete labeling of their cell bodies with anti-Mts1 than with anti-GFAP. Conversely, GFAP-IR processes were usually only partially labeled with anti-Mts1 (FIG. 1, B and D).

The levels Of Mts1-IR were considerably lower in the dorsal funiculus of L4–L5 and C3 as well as in the dorsal white matter of the brainstem compared to the ventral and lateral funiculi. Only some Mts1-positive profiles were observed (FIG. 1, E); there was no apparent difference in GFAP staining (FIG. 1, F).

Dorsal Root Injury

Figure 2:
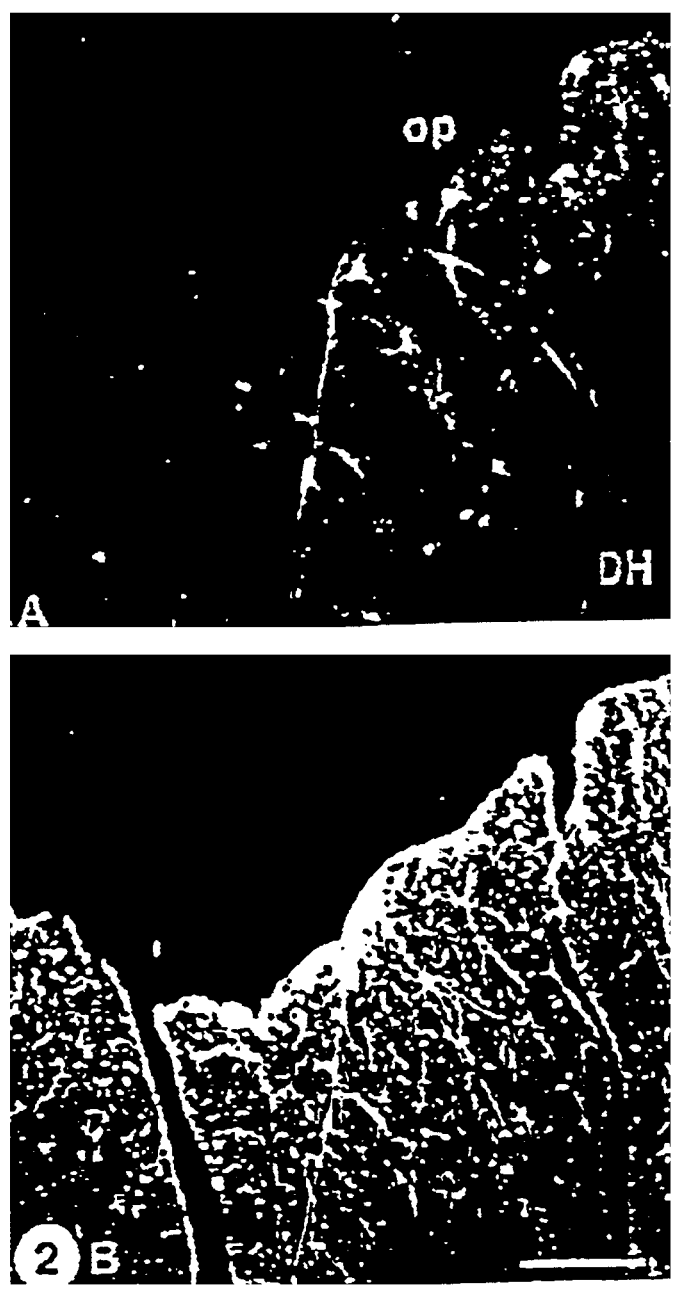
FIG. 2 depicts Mts1-IR (A) and GFAP-IR (B) in the dorsal funiculus and adjacent dorsal horn (DH) of L4 two days after unilateral transection of dorsal roots L4 and L5. There was a marked increase in Mts1-positive cell bodies and processes (A) in the white matter, and a concomitant increased expression of GFAP (B) on the operated side (right), but no Mts1-IR in the dorsal horn (DH). Bar=200 µm.
Figure 3:
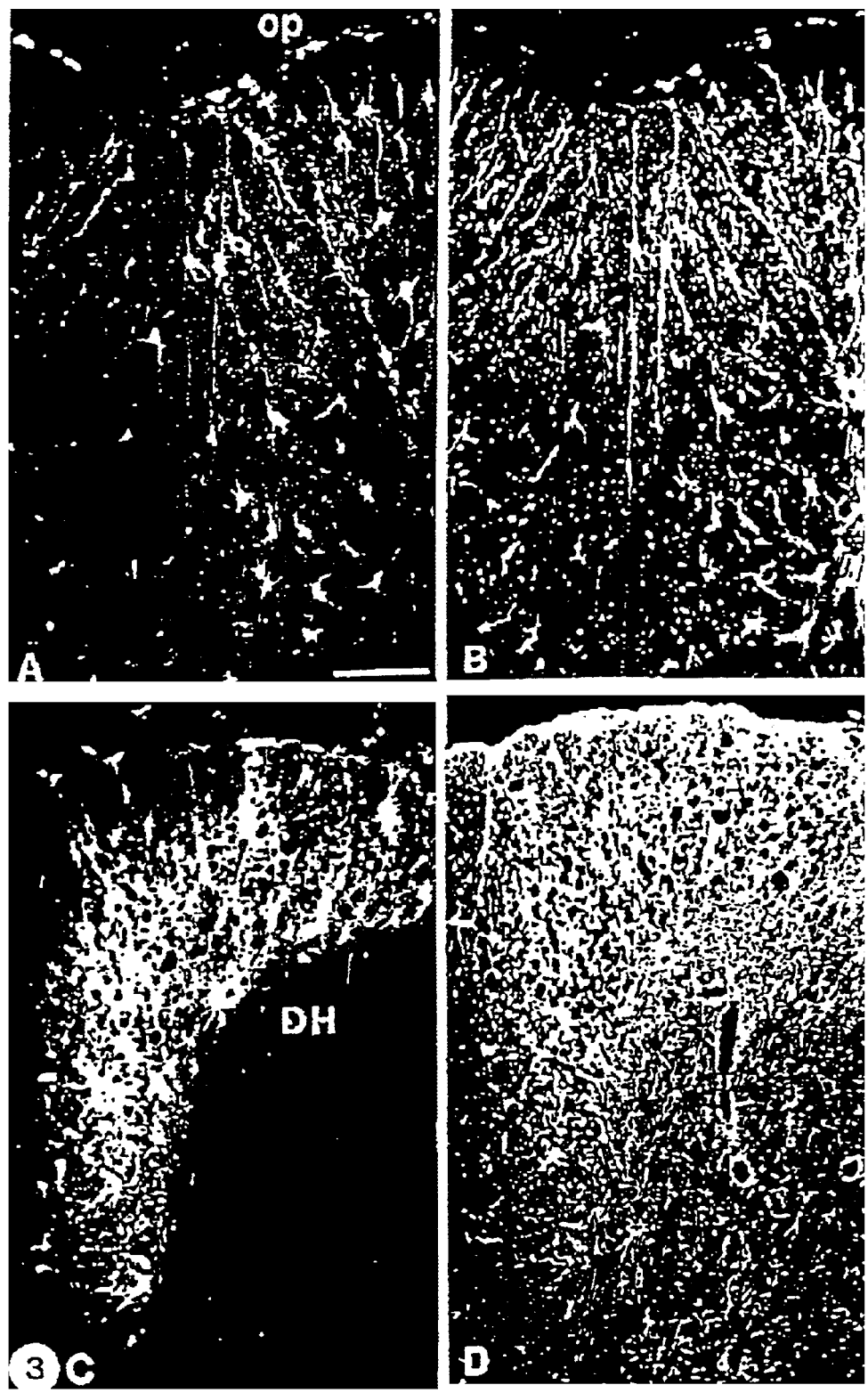
FIG. 3 depicts Mts1-IR (A,C) and GFAP-IR (B,D) in the dorsal funiculus of L4 one week (A,B) and two months (C,D) after unilateral transection of L4 and L5 dorsal roots. There was a marked upregulation in the expression of Mts1 (A,C) and GFAP (B,D) on the operated side (op). The dorsal horn (DH) was completely devoid of Mts1 staining (C), despite a prominent increase in GFAP-IR (D). Bar=100 µm.

Since the uninjured and injured sides of the spinal cord were next to each other, changes in Mts1-IR as a result of sciatic nerve or dorsal root transaction could be unambiguously identified. The first sign of an upregulation of Mts1-IR in the L4 dorsal funiculus was observed two days after dorsal rhizotomy (FIG. 2, A). This was paralleled by an increased staining for GFAP in the same area (FIG. 2, B). At this state, large Mts1-positive cells appeared in the area occupied by the injured primary sensory axons in the dorsal funiculus. The difference between the degenerating zone in the dorsal funiculus and the uninjured white matter gradually became stronger with increasing postoperative survival time (FIG. 3, A and B), and was very intense at two months after injury (FIG. 3, C and D). Importantly, the gray matter, including the dorsal horn termination area of the injured primary afferents, was always Mts1 negative, despite a marked up-regulation of GFAP-IR in the termination sites of the injured primary afferent fibers (FIG. 3, B and D).

Figure 4:
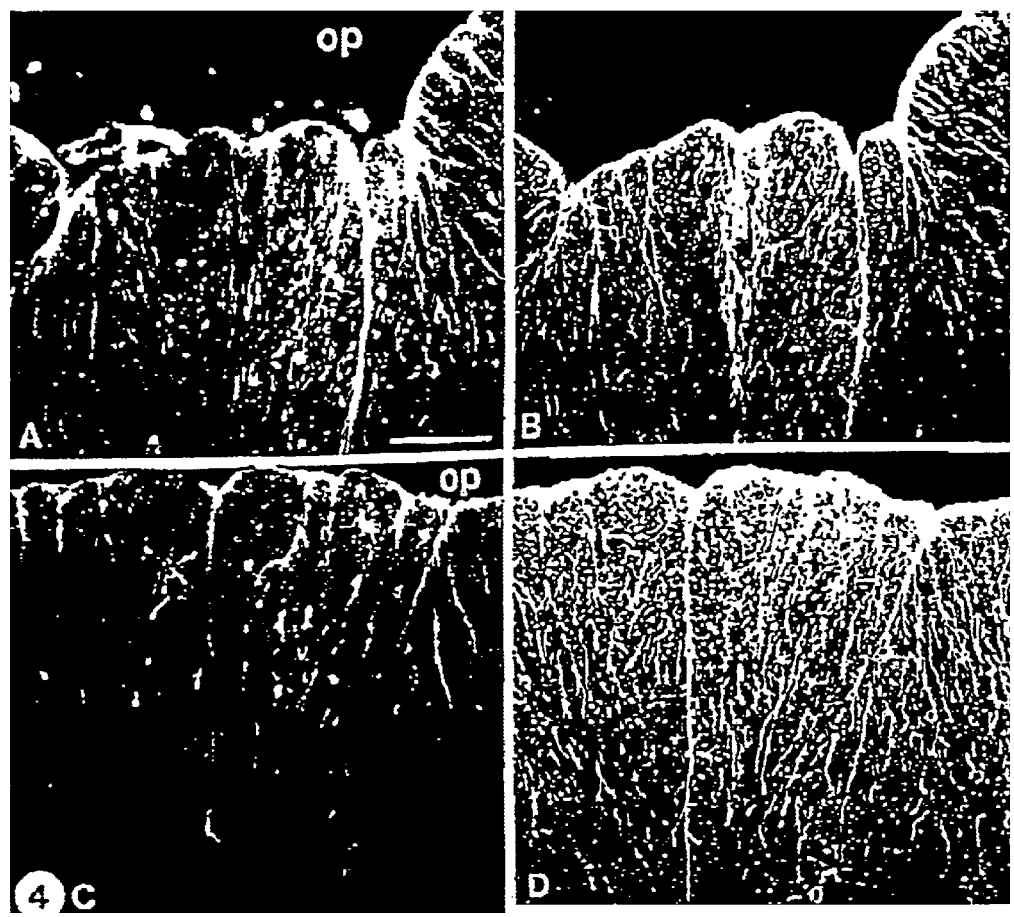
FIG. 4 depicts increased Mts1-IR (A,C) and GFAP-IR (B,D) in the gracile funiculus (A,B) and the dorsal funiculus of C3 (C,D) one week after ipsilateral injury to the L4 and L5 dorsal roots. Op=operated side. Bar=100 µm.

Increased immunoreactivity for Mts1 and GFAP also appeared along the central processes of the injured lumbar primary sensory afferents in the dorsal column of C3 and in the gracile nucleus. At one week after rhizotomy Mts1-IR was up-regulated concomitantly with GFAP-IR in the gracile funiculus and nucleus in the lower brainstem (FIG. 4, A and B) and in C3 in the circumscribed area of the dorsal funiculus containing the degenerating ascending primary sensory afferents (FIG. 4, C and D).

Double labeling with markers for Mts1 and for astrocytes (GFAP) or for microglia/macrophages (antibodies OX42 or ED1), showed overlap between Mts1-IR and GFAP-IR in the dorsal funiculus (FIG. 5, A), but none between Mts1- and OX42 or ED1-IR (FIG. 5, B).

Sciatic Nerve Injury

Figure 6:
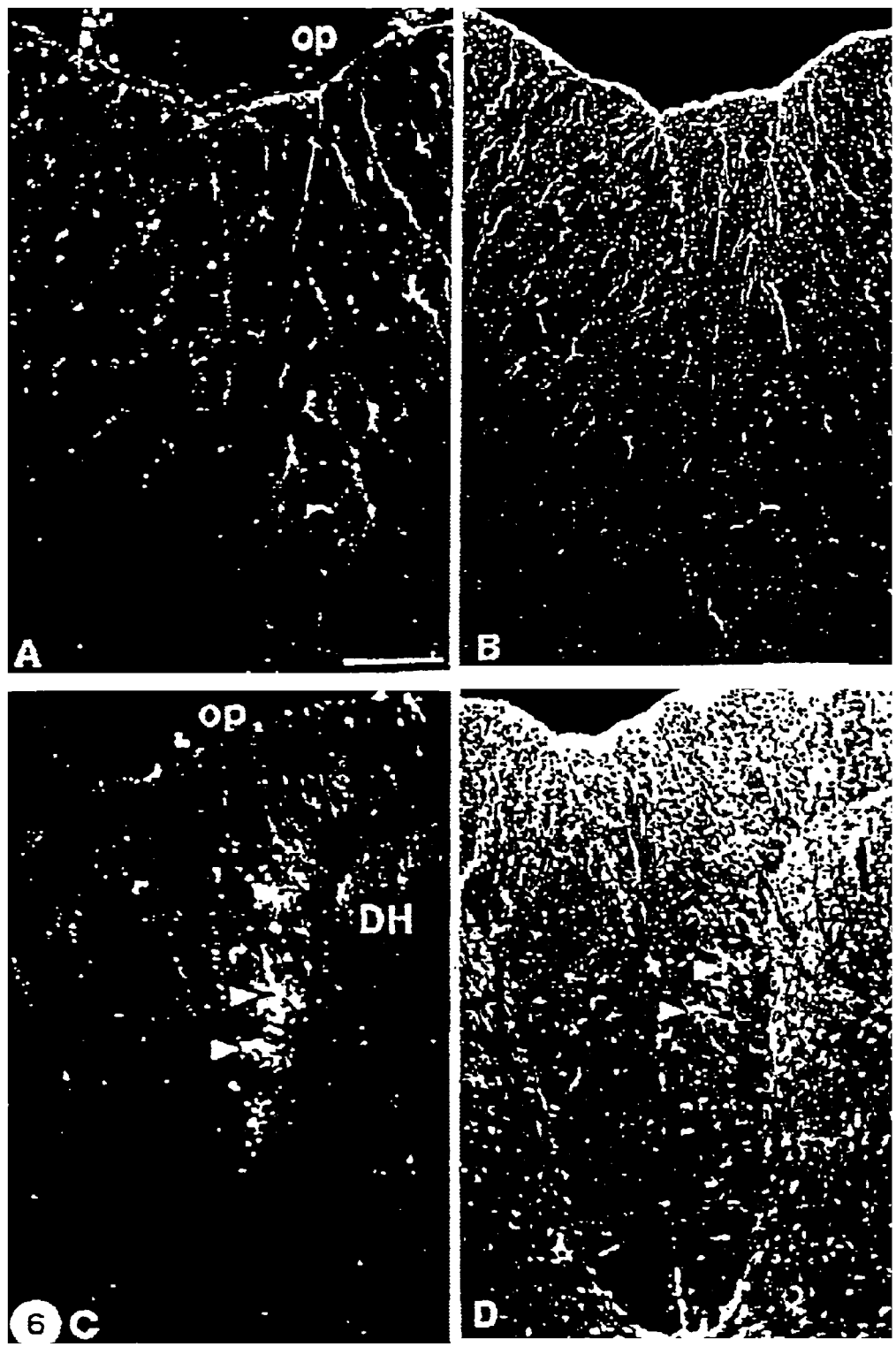
FIG. 6 depicts Mts1-IR (A,C) and GFAP-IR (B,D) in the dorsal funiculus of L4 one week (A,B) and two months (C,D) after unilateral transection of the sciatic nerve. There was an increased expression of Mts1 at both postoperative survival times (A,C). Mts1-IR was absent from the dorsal horn (C,DH). GFAP-IR was increased two months (D), but not one week (B) after injury compared to the unoperated side. Op=operated side. Bar=100 µm.

Mts1-IR in the ipsilateral dorsal funiculus was upregulated first at one week after sciatic nerve injury (FIG. 6, A) and showed a gradually increasing expression with longer survival times. However, at this postoperative time there was no increase in GFAP-IR (FIG. 6, B) in the dorsal funiculus, although there was an upregulation in the dorsal horn. The extent of Mts1-IR was never as great after sciatic nerve injury as after dorsal root lesions, even at the longest postoperative survival time of two months, when it coincided with an increased GRAP-IR (FIG. 6, C and D). The upregulation of Mts1 was always confined to the somatotopically appropriate area for sciatic nerve afferents in the dorsal funiculus, and did not include its most dorsomedial part, occupied by uninjured ascending sacral primary afferents, nor its ventralmost part occupied by the corticospinal tract. The gray matter was always free from Mts1-IR, despite an upregulation of GFAP-IR (FIG. 6, C and D). Double labeling with antibodies to Mts1 and with glial cell markers showed colocalization only with antibodies to GFAP (cf. FIG. 6, C and D).

EXAMPLE 2

Recombinant Mts1 Protein Stimulates Neurite Outgrowth in vitro

Murine Mts1 protein sequence was described by (Ebralidze et al., *Genes Dev.* 3, 1086–1092, 1989). cDNA fragments encoding the murine Mts1 protein and mutant Mts1 proteins containing a single mutation Y75F, a tyrosine deletion (del75) or cysteine/serine substitutions (4S) were cloned into pQE30 expression vector (QIAGEN, Inc., Ca.) and partially sequenced. Expression of recombinant $His_6$-tagged proteins was induced by isopropy-1-thio-β-D-galactopyranoside, and bacterial lysates were used for isolation of proteins according to the the manufacturer's protocol. Proteins were separated on SDS-PAGE, followed by Western blot analysis as described by Kriajevska et al. (*J. Biol. Chem.* 273: 9852–9856, 1998).

Hippocampus was isolated from wistar rat embryos at gestational day 18 and dissociated cells were obtained as descried by Maar et al. (*J. Neurosci. Res.* 47: 163–172, 1997). Briefly, hippocampal tissue was homogenized, trypsinized and washed in the presence of DNAse I and trypsin inhibitor. Hippocampal cells were seeded in 8-well LabTek coverslides at a density of $5 \times 10^3$ cells/$CM^2$, maintained in neurobasal medium supplemented with B27 supplement, 4 mg/ml bovine serum albumin (BSA), penicillin (100 U/ml) and streptomycin (100 µg/ml). Cells were grown for 24 h in a humidified atmosphere with 5% $CO_2$.

The neurogenic effect of Mts1 was analyzed-by computer-assisted morphometry. The embryonic hippocampal neurons of 18-day rats were cultured with and without the Mts1 protein at low cell density in serum free defined medium. Cells were then fixed in 4% paraformaldehyde and stained for 20 min in Commassie blue R250 (4 g/l in 45% v/v ethanol and 45% v/v acetic acid). Coverslides were observed in a Nikon Diaphot 300 inverted microscope using phase contrast optics (Nikon Plan 20×). Video recording was made with a CCD video camera (Burle, USA). 512×512 pixel images were stored in a computer using the PRIGRA software package (Protein Laboratory, University of Copenhagen). To measure neurite outgrowth from hippocampal neurons a simple procedure developed at the Protein Laboratory and based on stereological principles was used.

Briefly, by means of the software package "ProcessLenghth" (Protein Laboratory, University of Copenhagen), an unbiased counting frame containing a grid with a certain number of test-lines was superimposed on images of the cell cultures. The number of intersections of cellular processes with the test-lines was counted and related to the number of cell bodies, thereby allowing qualification of the total neurite length per cell by means of the equation, $L=\pi/2 \times d \times J$, in which L is the neuritic length in micrometers, d is the vertical distance between two test lines and J is the number of intersections between the test lines and the neurites.

Figure 7A:
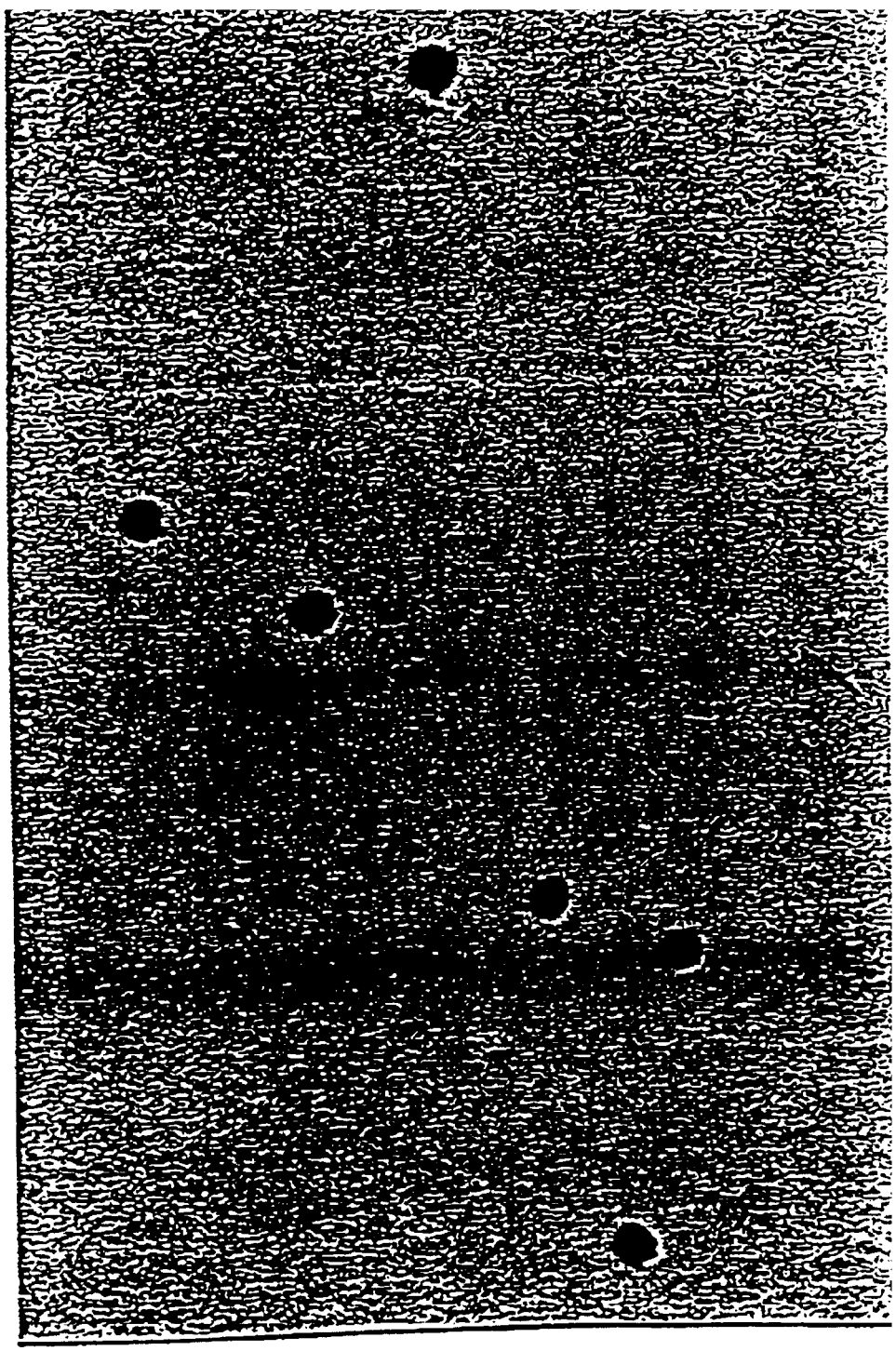
FIG. 7A is a phase contrast micrograph of a 24 h low-density culture of dissociated hippocampal cells of rat embryos (E18).
Figure 7B:
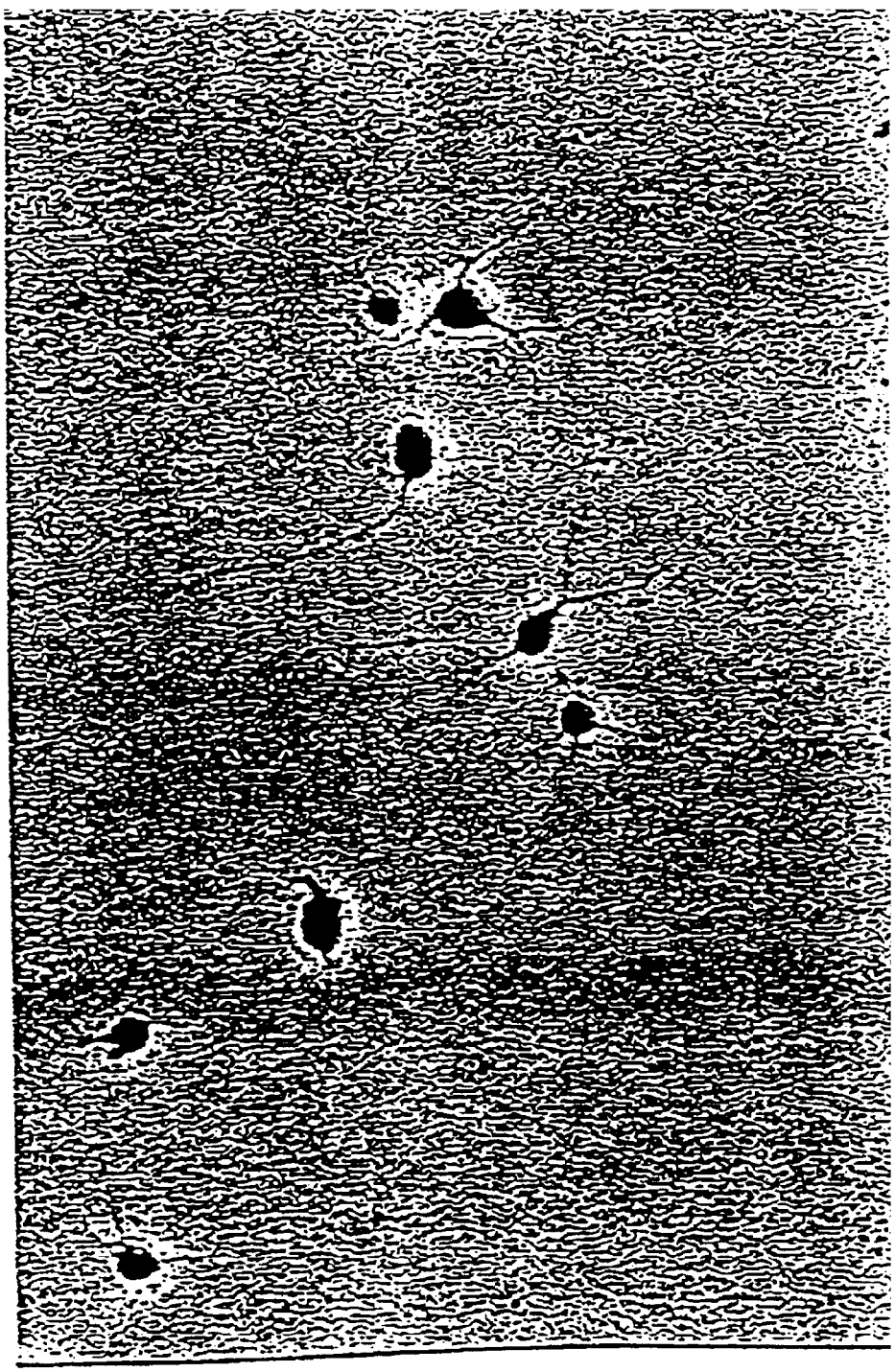
FIG. 7B is a phase contrast micrograph of a 24 h low-density culture of dissociated hippocampal cells of rat embryos (E18) grown in the presence of 5 µM recombinant Mts1/S100A4 protein.
Figure 7C:
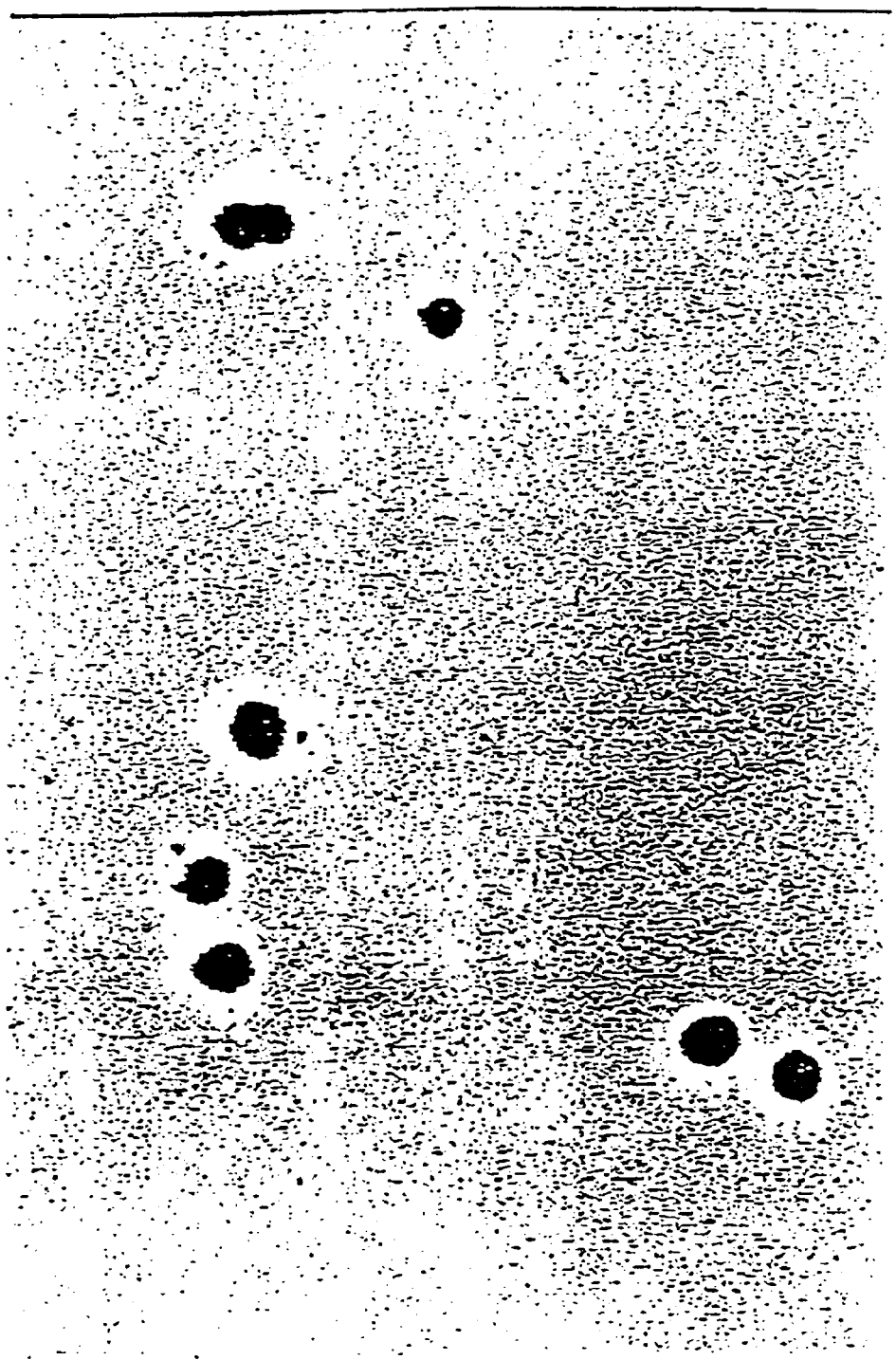
FIG. 7C is a phase contrast micrograph of a 24 h low-density culture of dissociated hippocampal cells of rat embryos (E18) grown in the presence of 5 µM recombinant His-tagged 200aa C-terminal peptide of myosin heavy chain.

It was observed that hippocampal neurons cultured without the Mts1 protein did not differentiate by extending processes (FIG. 7A). Treatment of hippocampal neurons with the recombinant His-tagged wt Mts1 protein of 5 $\mu$M for 12 hours had a robust effect on their differentiation (FIG. 7B). Neurons extended multiple, long branching processes. Cell cultures treated with the recombinant His-tagged 200aa C-terminal peptide of the myosin heavy chain (Kriajevsta et al., J. Biol. Chem 273: 9852–56, 1998) for 24 h, revealed minimal morphological changes in comparison to control cultures (FIG. 7C).

Figure 8A:
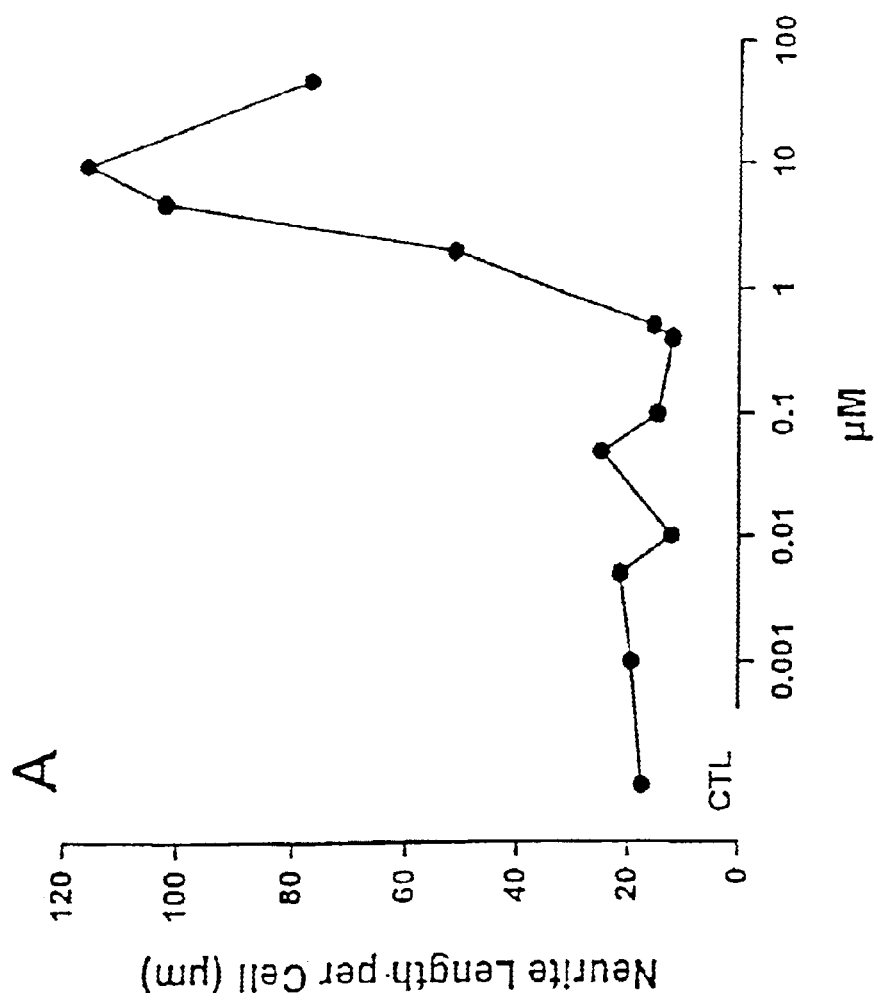
FIG. 8A depicts the dose-dependent effect of Mts1/S100A4 on neurite outgrowth in primary cultures of dissociated rat hippocampal cells. Cultures were grown in the presence of various amounts of the recombinant protein for 24 h, and neurite length per cell was measured.

The stimulation of neurites outgrowth by the recombinant Mts1 protein was time- and dose-dependent. Mts1 was effective in the micromolar concentration range, with the maximal growth-stimulatory activity being 5–10 $\mu$M (FIG. 8A). Mts1 treatment increased the total length of neurite per cell when compared to the control, as well as the number of neurites (7 fold), the length of the longest neurite (14 fold) and the number of branches (25 fold) per cell (Table 1).

TABLE 1

Neurite Induction in Hippocampal Neurons in Vitro Following Treatment with the Recombinant Mouse Mts1/S100A4 Protein

|  | Neurites per cell | Total neurite length per cell ($\mu$M) | Length of the longest neurite per cell ($\mu$M) | Neurite branches per cell |
| --- | --- | --- | --- | --- |
| Control | 0.29 ± 0.06 | 12.6 ± 1.3 | 3.43 ± 0.5 | 0.013 ± 0.01 |
| Mts1 (5 $\mu$M) | 2.12 ± 0.3 | 93 ± 17 | 49.5 ± 1.5 | 0.36 ± 0.08 |

Figure 8B:
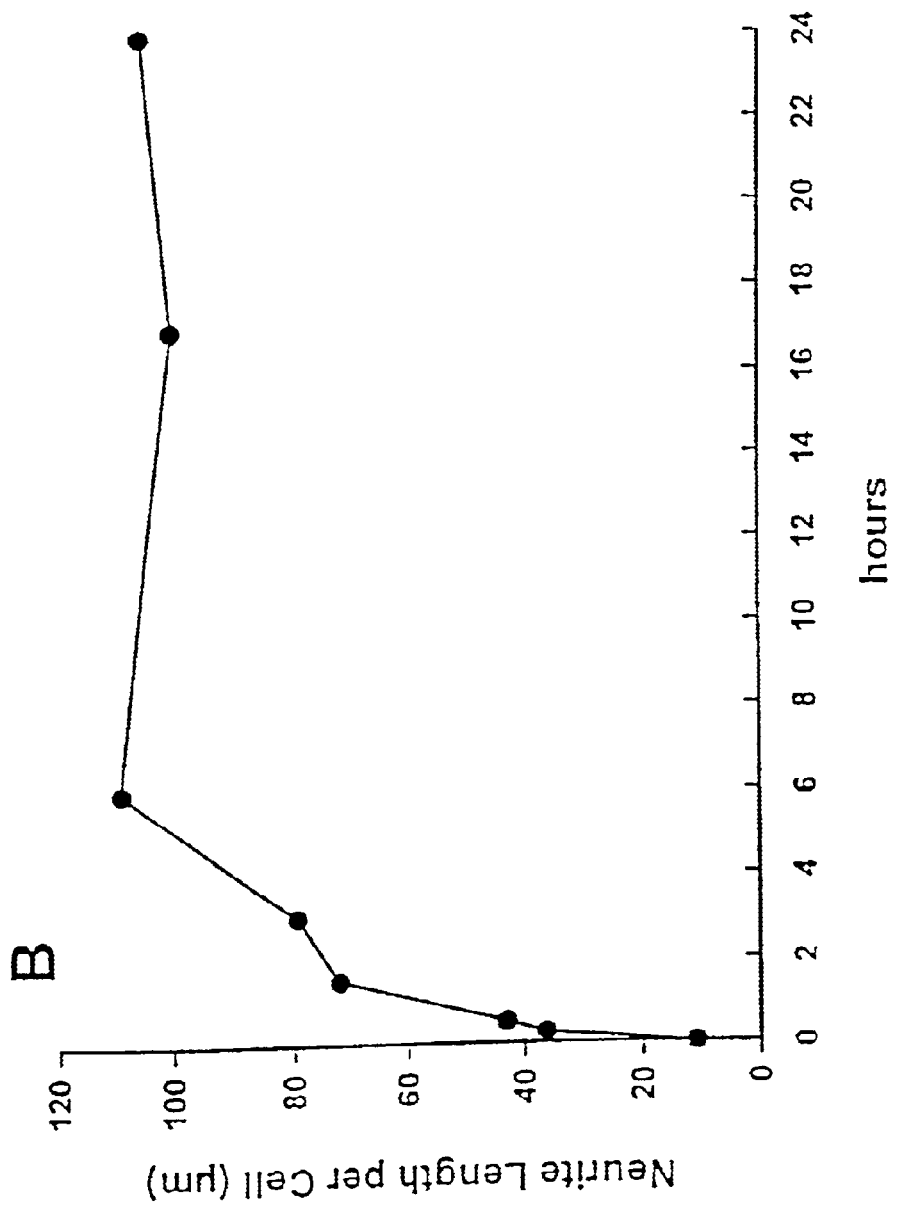
FIG. 8B depicts the time-dependent effect of Mts1/S100A4 on neurite outgrowth in primary cultures of dissociated rat hippocampal cells. Hippocampal cells were seeded and allowed to attach for 1 h after which recombinant Mts1/S100A4 was added to the culture (time 0). At various time points afterwards, Mts1/S100A4 was removed by changing culture medium and neurite length per cell was measured 24 h after addition of the protein.

The duration of the Mts1 protein treatment required for hippocampal cells to extend neurites was also determinaed. In these experiments, Mts1 was added at the time (time 0) when seeded cells were allowed to attach for 1 h. At various time points Mts1 was removed by changing culture medium, and neurite outgrowth was measured 24 h later. Cells exposed to the Mts1 protein for 15–30 min already displayed a 4-fold increase in the total length of neurites when compared to control cells. The response of cells exposed to Mts1 for more that 1.5 h was obvious and indistinguishable after further incubation for 4, 6, 16 or 24 h, respectively (FIG. 8B). These data indicate that continuous exposure of cells to Mts1 for 24 h is not required and that there is an early period, approximately 1–1.5 hour, when the presence of Mts1 is essential for the maximal neurite outgrowth.

Figure 8C:
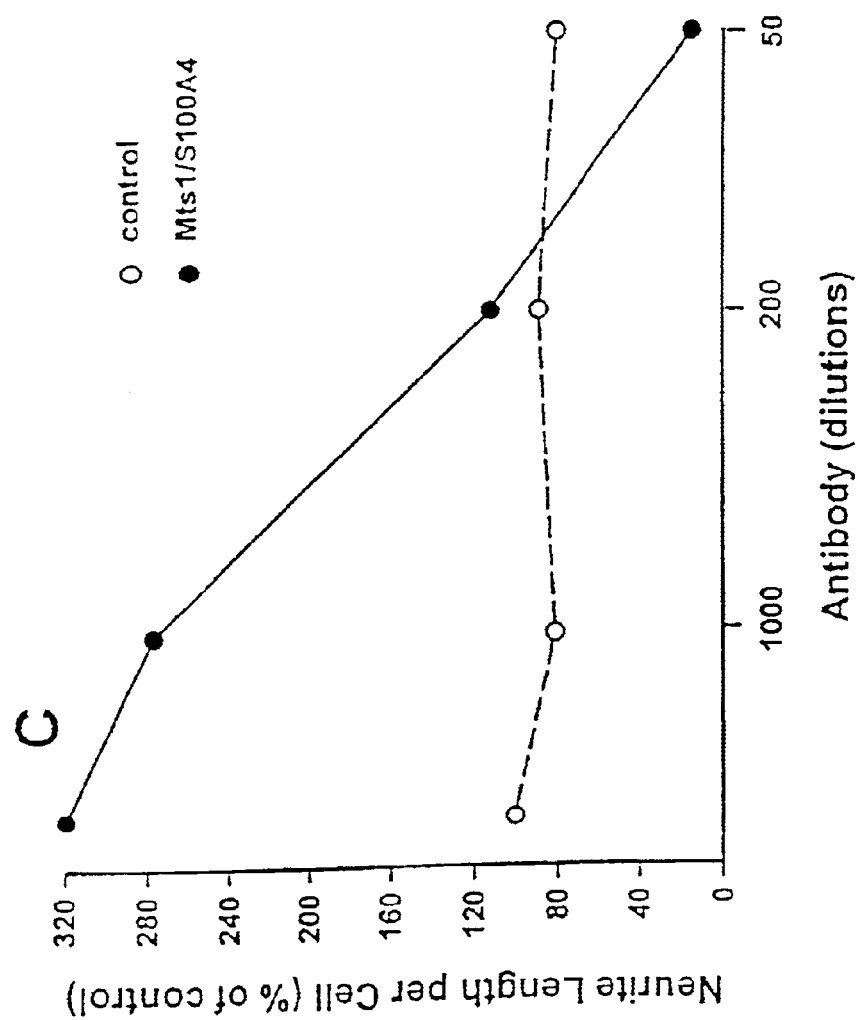
FIG. 8C depicts the specificity of the Mts1/S100A4 effects on neurite outgrowth in primary cultures of dissociated rat hippocampal cells. Hippocampal cells were grown for 24 h in the presence of 5 µM Mts1/S100A4 and rabbit polyclonal anti-Mts1 antibodies at various dilutions. The length of neurites in treated cultures is expressed as a percentage of the length of neurites in control cultures.

The specificity of Mts1 neurogenic activity was tested by examining the activity of the Mts1 protein after incubation with antibodies to Mts1. The Mts1 protein was mixed with serial dilutions of polyclonal anti-Mts1 antibodies in growth medium, incubated for 1 h and applied to hippocampal cells. FIG. 8C shows that incubation of Mts1 with antibodies directed against Mts1 reduced the neurite extension in a reverse proportion to the antibodies dilutions. Incubation of Mts1 with control IgG, anti nonmuscle myosin or normal rabbit serum, did not reduce the response.

Figure 9A:
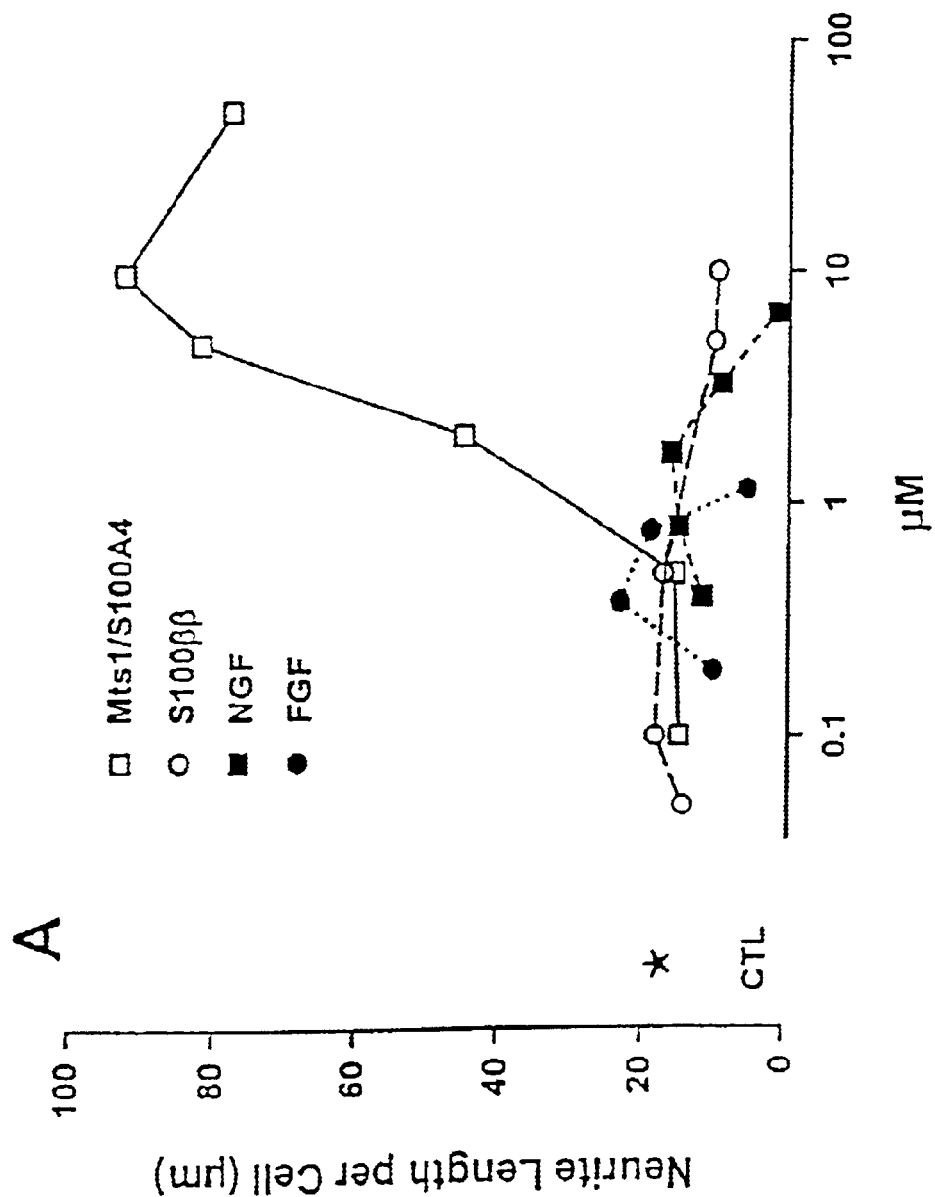
FIG. 9A depicts the effects of Mts1/S100A4, S100β, NGF and FGF on neurite outgrowth from hippocampal neurons. Cultures were grown for 24 h in the absence or in the presence of Mts1/S100A4, S100ββ, NGF or FGF at indicated concentrations. Results of a typical experiment are shown.

The neurogenic activity of Mts1 was compared with the activities of other neurotrophic growth factors, including FGF (Fibroblast Growth Factor), NGF (Nerve Growth Factor) and members of S100 $Ca^{2+}$-binding protein—S100$\alpha$ and S100$\beta$. Neurite outgrowth from hippocampal neurons was not stimulated by FGF, NGF or S100$\beta$ (FIG. 9A). Treatment with S100$\alpha$ did not affect hippocampal cultures either. Moreover, NGF actually inhibited neurite outgrowth at high concentrations (5–10 $\mu$M).

Figure 9B:
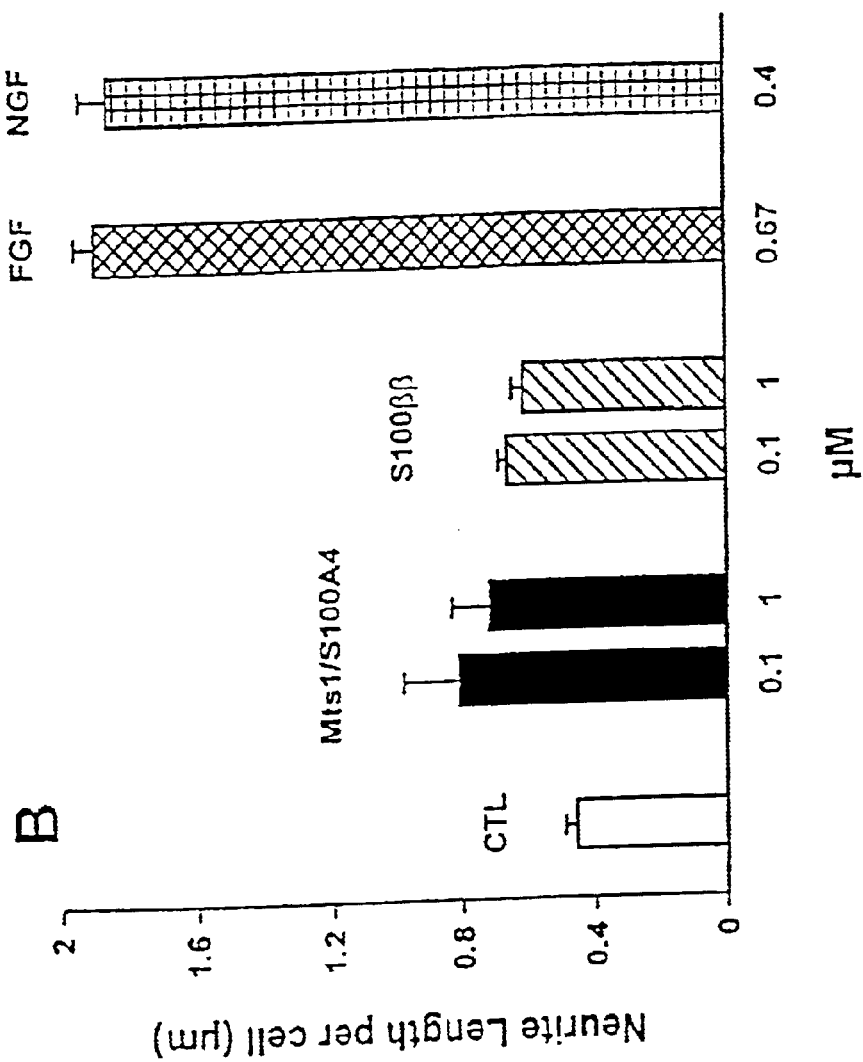
FIG. 9B depicts the effects of Mts1/S100A4, S100β, NGF and FGF on neurite outgrowth from PC12-E2 cells. Four individual experiments were performed. Results are given as mean±SEM.

To assess the possibility that lack of responsiveness of hippocampal cells to FGF, NGF, and S100$\beta$ reflected cell specific activity of these neurotropic factors, PC-12 cells were tested. As shown in FIG. 9B, Mts1 and S100$\beta$ showed equal neurite outgrowth stimulatory activity in the PC-12 cells. As shown in FIG. 9B, Mts1 and S100$\beta$ showed equal neurite outgrowth stimulatory activity in the PC-12 cell system that was twice as high compared with that in the hippocampal cells. In contrast, neurite extension effect of FGF and NGF on cultured PC-12 cells was significantly higher that on hippocampal cells. The data indicate that the stimulatory effects of different neurotrophic factors are cell specific, and Mts1 is a potent activator of neurites outgrowth of hippocampal cells.

EXAMPLE 3

Structural Requirements for the Mts1 Neurite Outgrowth Promoting Activity

To determine the structural elements in the Mts1 protein that are required for promoting neurite outgrowth, three Mts1 mutatant proteins were tested. In one of the mutants, Tyrosine75 was substituted to Phenylalanine (Y75F). In the other mutant Tyrosine75 was deleted (del75). It was found that Del75 could not form dimers in the yeast two-hybrid system, while the Y75F mutant formed perfect dimers in the yeast with an efficiency even higher than wt Mts1.

Figure 10:
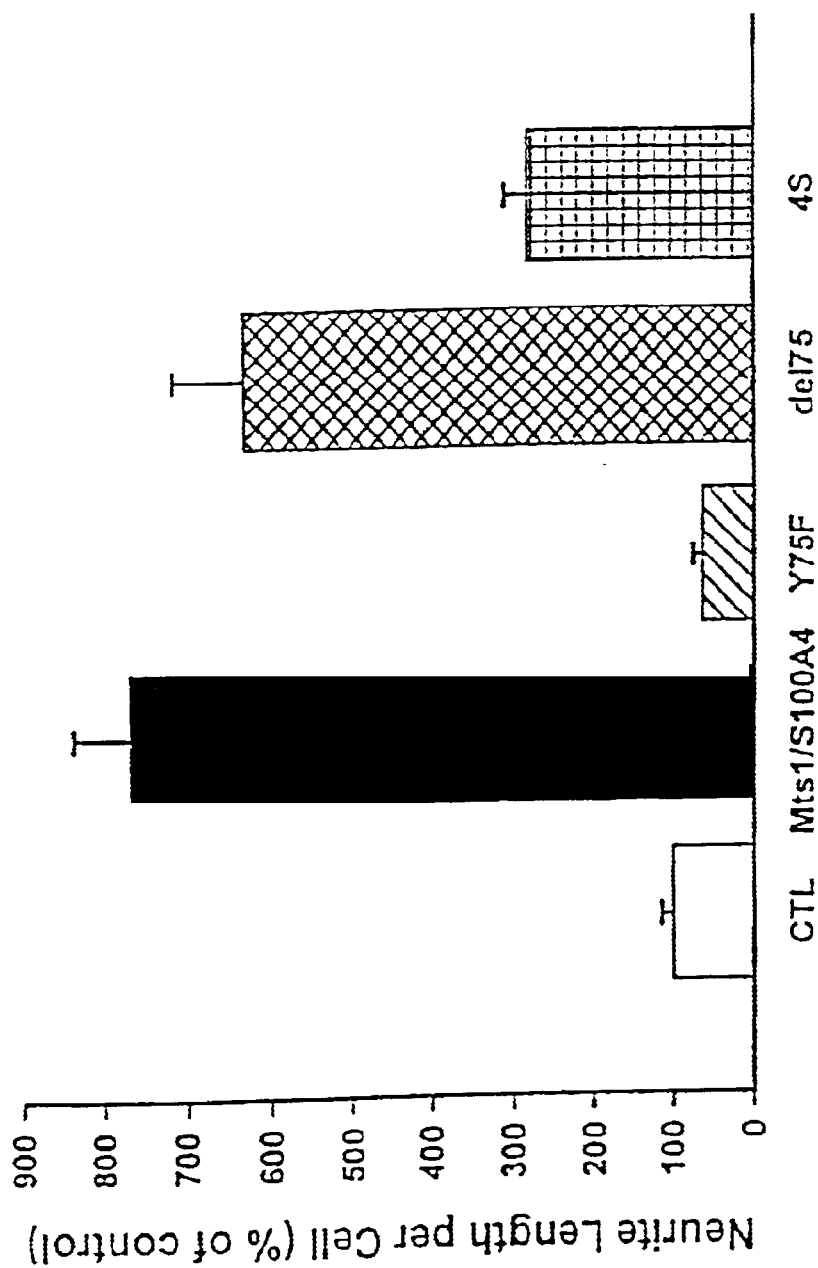
FIG. 10 depicts the neurogenic effects of the wild type and mutatnt Mts1/S100A4 proteins. Hippocampal cells were grown for 24 h in the presence of 5 µM mouse recombinant Mts1/S100A4 or in the presence of 5 µM of the Mts1 mutated proteins. The length of neurites in treated cultures is expressed as a percentage of the length of neurites in control cultures. Four individual experiments were performed. Results are given as mean±SEM.

When these two mutant Mts1 proteins were tested in the in vitro system of cultured hippocampal cells, it was found that Y75F did not stimulate neurite outgrowth from hippocampal cells. In contrast, cells incubated with del75 for 24 h displayed abundant neurites, although the degree of neurite outgrowth was generally lower than that obtained with the wild type Mts1 (FIG. 10).

To examine whether disulfide bonds contribute to the neurogenic activity of the Mts1 protein, the Mts1 mutant termed 4S was used, in which all four cysteines (at positions 76,81,86 and 93) of the Mts1 protein were changed to serines. It was found that 4S was able to form dimers in the yeast two hybrid system, but unable to interact with the heavy chain of myosin in a gel overlay assay. When tested for the ability to stimulate neurite outgrowth, the 4S mutant showed 40% of the neurogenic activity of that of wt Mts1 (FIG. 10).

In order to determine which conformational forms of Mts1 were active with regard to neurogenic activity, size-exclusion chromatography (SEC) of the recombinant Mts1 and the Mts1 mutants were performed. A Superdex75 column (1.5 cm²×90.0 cm) was equilibrated with a TND buffer (50 mM Tris-HCl, 150 nM NaCl, 1 mM DTT, pH 7.5) with and without 5 mM CaCl₂. The column was calibrated for molecular weight determinations using gel filtration chromatography standard (Bio-Rad). The standard proteins included Vitamin B-12 (MW 1.35 kDa), equine myoglobin (MW 17.0 kDa), chicken ovalbumin (MW 44.0 kDa), bovine gamma globulin (MW 158.0 kDa), thyroglobulin (MW 670.0 kDa). 1 ml of the mixed proteins standard (2 mg/ml) was loaded onto the column and 3 ml fractions were collected and monitored with $A_{280}$ readings. Dextran blue was applied to the column to determine its void volume. The $K_{av}$ values were determined for each protein and plotted versus the log of the molecular weight of the standard $K_{av}=(V_e-V_0)/(V_t-V_o)$ ($V_e$ is the elution volume at the peak apex, $V_o$ is the void volume, and $V_t$ is the total column volume; see Landar et al., *Biochim. Biophys. Acta* 1343: 117–129, 1997).

Figures 1, 11A:
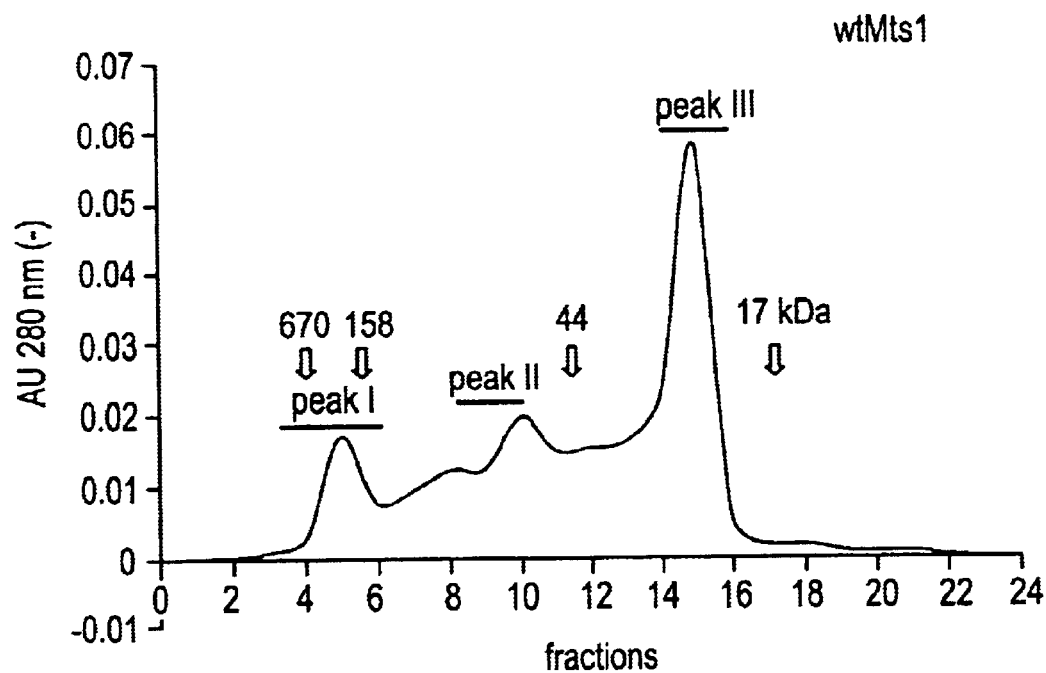
FIGS. 11A–11C depict the profiles of the recombinant wild type (wt) Mts1 protein (11A) and two mutants, Y75F (11B) and del75 (11C) off size exclusion chromatography (SEC). One milliliter of each protein (2 mg/ml) was chromatographed on a Superdex G75 column. The column was equilibrated with TND, eluted (1 ml/min) with the same buffer and 3-ml fractions were collected. Results of a typical experiment are shown. Relative positions of peak I, II and III are indicated with respect to molecular weight markers: thyroglobulin—670 kDa; bovine gamma globulin—158 kDa; chicken ovalbumin—44 kDa; equine myoglobin—17 kDa. Inserts—fractions of each peak were combined and assayed for neurite outgrowth activity on hippocampal cells. The length of neurites in treated cultures is expressed as a percentage of the length of neurites in control cultures.
Figures 2, 11A:
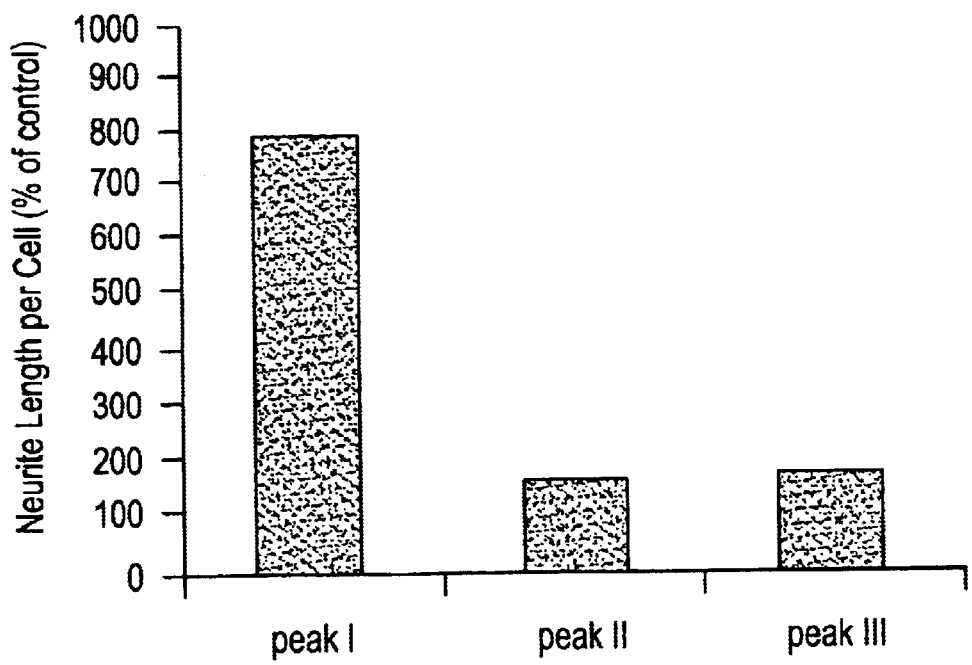

1 ml samples of the Mts1 protein or mutants were applied onto the column and a $K_{av}$ value was determined in each case. The molecular weight of Mts1 was determined by comparing its $K_{av}$ value to those found for the standard proteins. Gel filtration chromatography experiments were performed under different conditions: presence of reducing agent, 2 mM calcium or 2 mM EDTA, 0.5 M or 0.15 M NaCl. The fractions were assayed by both SDS-PAGE and the neurite outgrowth test. Under either condition, the eluted material showed a broad profile of distribution with molecular masses ranging approximately from 30 to 200 kDa. (FIG. 11A). Approximately half of the recombinant wild type Mts1 protein was eluted as a high molecular weight complex. The distinct peak of a dimer was consistently detected among different batches of freshly prepared recombinant Mts1, whereas the elution profile of a higher molecular mass material was less reproducible and varied in different Mts1 preparations.

Figures 1, 11B:
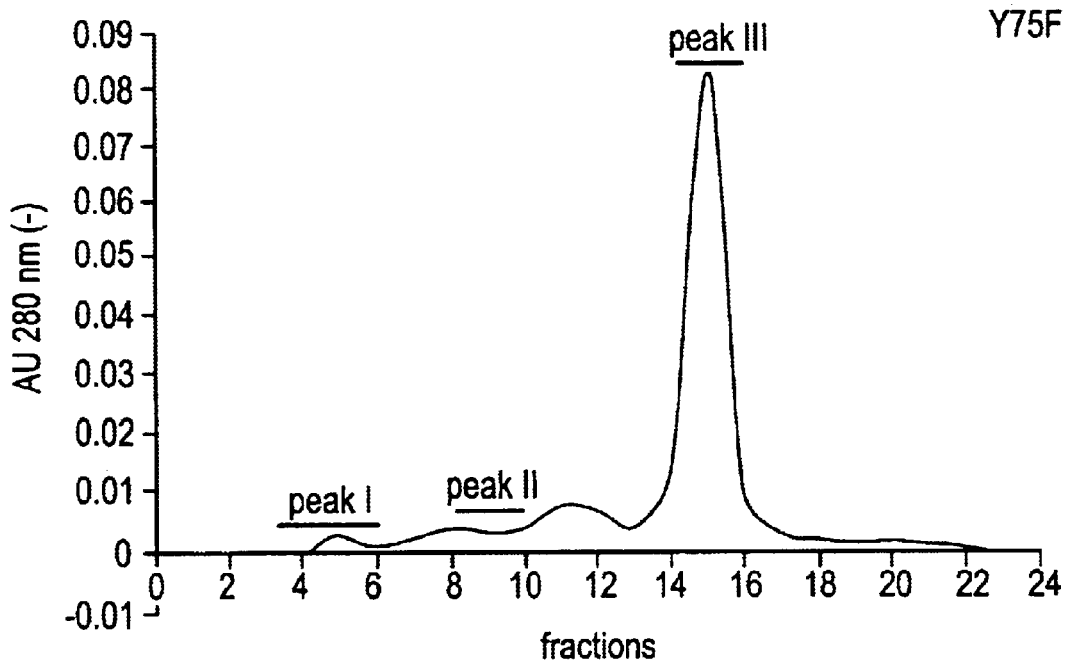
Figures 2, 11B:
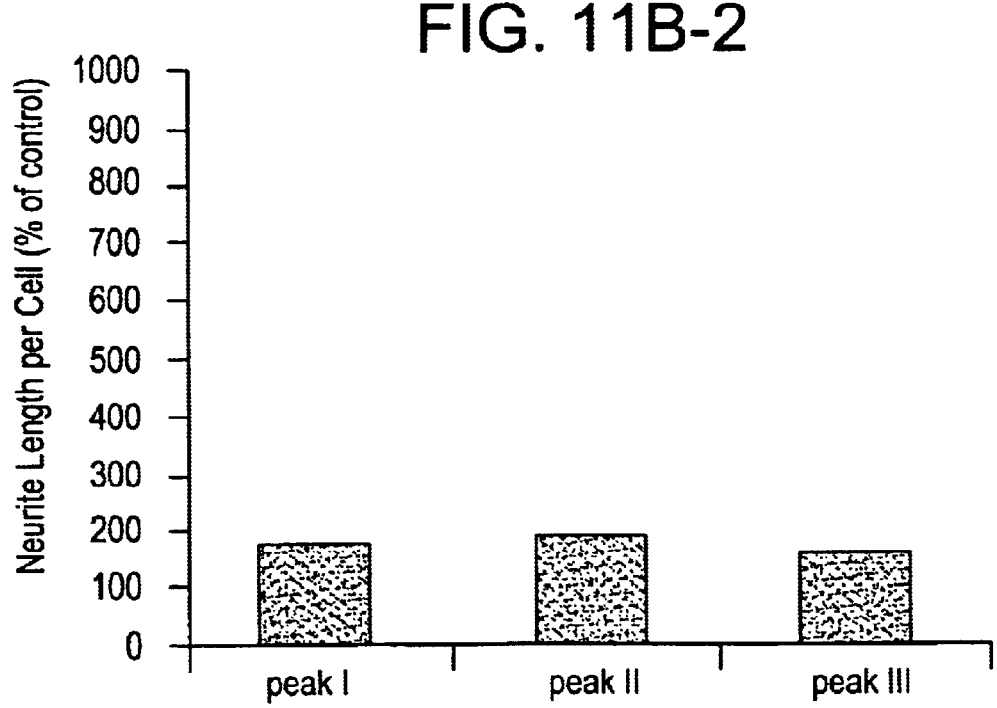

The elution profile of the Y75F mutant was different as shown in FIG. 11B. 85% of the Y75F protein was eluted from gel filtration columns as a single peak with a molecular weight of a dimer, and 15% as materials of higher molecular-weights ranging from 30 to 100 kDa (FIG. 11B). The elution profile of the mutant del75 was different from either the wild type Mts1 or the Y75F mutant protein. Major part of the del75 protein was eluted as materials of high molecular weights ranging approximately from 40 kDa to 200 kDa.

It was further found that the elution profiles of all proteins were not influenced by alterations in the Ca++ concentration, nor by changes from reducing to non-reducing conditions, nor by changes in ionic strength.

Different fractions eluted from the column, named peaks I, II and III for all three tested proteins, were analyzed for the presence of Mts1 by Coomassie staining and Western blot analysis (FIG. 11D). The Mts1 protein under reducing condition yielded one 11 kDa band in all analyzed fractions. Western blot analysis with affinity purified antiserum confirmed the Mts1 origin of the bands described as monomer. SDS gel patterns of the two mutant proteins were similar to Mts1.

Figures 1, 11C:
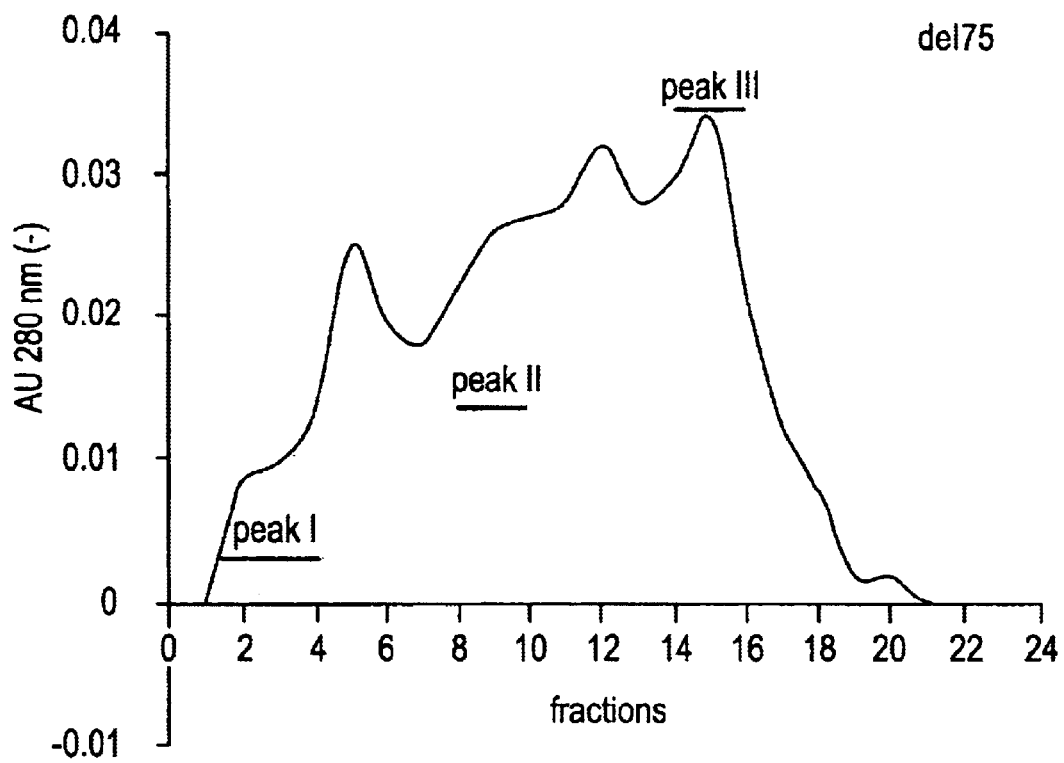
Figures 2, 11C:
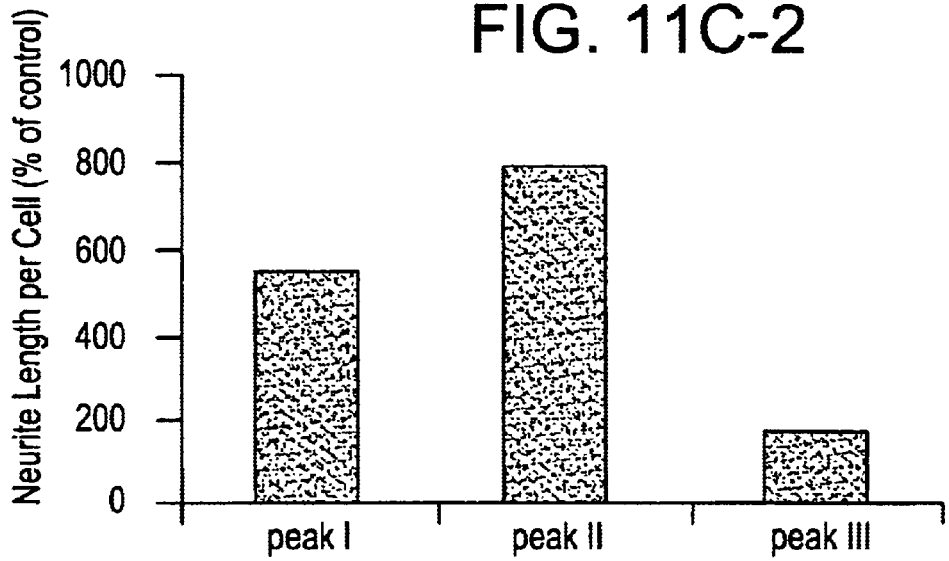

The relative contribution to the neurogenic activity of different forms of the Mts1 protein, eluted from the SEC column as peaks I, II and III, was tested. Inserts in FIGS. 11A–11C show that high molecular weight complexes (100–200 kDa) of wt Mts1 as well as del75 mutant stimulated neurite outgrowth. Peak I demonstrated the highest activity. The neurogenic activity of the protein in peak II was less reproducible and accounted for 30% of the activity observed in the peak I. Dimeric forms (peak III) of wt Mts1 and two Mts1 mutants (Y75F and 4S) showed no activity at any dose tested. The data indicate that the ability to stimulate neurite extension is attributed to the polymeric fraction of the Mts1 molecules with unidentified structural conformations.

In order to monitor the polymerization of Mts1 and to determine the molecular weight of the polymers more precisely, the recombinant Mts1 protein was analyzed by Dynamic Light Scattering, a standard technique for determination of the molecular weight of globular proteins (Berne et al., *Dynamic Light Scattering*, Chap. 5, Wiley, N.Y., 1976). The diffusion coefficient ($D_t$) and calculated molecular weight were determined with DLS using Dyna Pro 801 Molecular Sizing Instrument (Protein Solutions Inc.). All readings were recorded at 18° C. All samples were filtrated through a 0.02 µm membrane (Whatman) before measurements. Protein solutions were injected into a 25 µl cell (cuvette) and illuminated by a 25W 750 nm wave length laser. Data were fitted with the Dynamics Version 4.0 software package. The molecular weight (M.W.) was calculated by two alternative models. According to the first model, M.W. was estimated from the hydrodynamic radius ($R_h$) using an empirically derived relationship between the $R_h$ and M.W. values for a number of well-characterized globular proteins in a buffered aqueous solution, assuming that the protein holds a standard globular shape and density. In the second model, the volume-shape-hydration relationship was used, in which model the calculation required the values of the hydrodynamic size, partial specific volume, and frictional ratio. (The value of partial specific volume (V) is 0.707 in the absence of $Ca^{2+}$ and V increases when $Ca^{2+}$ is added (Mani et al., *FEBS Lett*. 166, 258–262, 1984). The value of frictional ratio (f) is 1.45 and f decreases when $Ca^{2+}$ is added (Matsuda et al., *Biochem, and Mol. Biol. International* 30, 419–424, 1993). In Table 2 it can be seen that the recombinant Mts1 protein at a concentration 1.5 mg/ml had a broad spectrum of molecular weights ranging from 28.9 kDa for dimer, 47.2 kDa for tetramer, and up to 143.0–200.0 kDa for polymeric molecules.

TABLE 2

| | Dynamic Light Scattering | | | |
|---|---|---|---|---|
| Parameters Oligomeric State | $D_t$ (1e-9*cm/s^2) | $R_h$ nm | M.W (kDa) First Model | M.W (kDa) Second Model |
| Dimers | 785 | 2.56 | 28.9 | nd |
| Tetramers | 636 | 3.16 | 47.2 | nd |
| Oligomers | 398 | 4.99 | 143.0 | 200.0 |

We claim:

1. An isolated multimeric Mts1 protein complex, comprising at least three molecules of an Mts1 protein.

2. The isolated multimeric Mts1 protein complex of claim 1, having a Mw in the range of about 30 kD to about 200 kD.

3. The isolated multimeric Mts1 protein complex of claim 1, wherein said Mts1 protein is a wild type Mts1 protein.

4. An isolated multimeric Mts1 protein complex, comprising at least three molecules of Mts1 -del75.

5. The isolated multimeric Mts1 protein complex of claim 1, wherein said Mts1 protein is of a mammalian origin.

6. A pharmaceutical composition comprising the isolated complex of claim 1, and a pharmaceutically acceptable carrier.

7. The pharmaceutical composition of claim 6, wherein said pharmaceutically acceptable carrier is liquid, semi-solid, or solid.

8. The pharmaceutical composition of claim 6, further comprising a neurotropic factor.

9. The pharmaceutical composition of claim 8, wherein said neurotropic factor is selected from the group consisting of bFGF, aFGF, CNTF, NGF, BDNF, GDNF, NT3, NT4/5, IGF-1 and IGF-II.

10. The isolated multimeric Mts1 protein complex of claim 1, wherein said Mts-1 protein is a human Mts-1 protein.

11. The isolated multimeric Mts1 protein complex of claim 10, wherein said human Mts-1 protein comprises the sequence as set forth in SEQ ID NO: 1.

12. The isolated multimeric Mts1 protein complex of claim 1, wherein said Mts-1 protein comprises the sequence as set forth in SEQ ID NO: 2.

13. An isolated multimeric Mts1 protein complex, comprising at least three molecules of human Mts1-del75.

* * * * *